US008481306B2

(12) United States Patent
Dong et al.

(10) Patent No.: US 8,481,306 B2
(45) Date of Patent: Jul. 9, 2013

(54) METHODS FOR LIGATION INDEPENDENT CLONING OF DNA

(75) Inventors: Fenggao Dong, Chesterfield, MO (US); Brian M. Hauge, Wildwood, MO (US); Christopher Oggero, Valmeyer, IL (US)

(73) Assignee: Monsanto Technology LLC, St. Louis, MO (US)

( * ) Notice: Subject to any disclaimer, the term of this patent is extended or adjusted under 35 U.S.C. 154(b) by 846 days.

(21) Appl. No.: 11/298,234

(22) Filed: Dec. 9, 2005

(65) Prior Publication Data

US 2006/0147961 A1 Jul. 6, 2006

Related U.S. Application Data

(60) Provisional application No. 60/634,779, filed on Dec. 9, 2004.

(51) Int. Cl.

| | |
|---|---|
| ***C12N 15/82*** | (2006.01) |
| ***C12N 15/87*** | (2006.01) |
| ***A01H 1/00*** | (2006.01) |

(52) U.S. Cl.
USPC .......................... 435/320.1; 800/286; 800/285

(58) Field of Classification Search
None
See application file for complete search history.

(56) References Cited

U.S. PATENT DOCUMENTS

| | | | | |
|---|---|---|---|---|
| 6,495,318 | B2 * | 12/2002 | Harney | 435/6 |
| 2003/0150017 | A1 * | 8/2003 | Mesa et al. | 800/279 |
| 2005/0176670 | A1 * | 8/2005 | Huang et al. | 514/44 |

OTHER PUBLICATIONS

Wesley et al. 2001, The Plant Journal 27:581-590.*
Hussam et al., Advancing usracil-excision based cloning towards an ideal technique for cloning PCR fragments Nucleic Acids Research, 2006, pp. 1-8 of e122, vol. 34, No. 18.
J A Vroom and C L Wang, Modular construction of plasmids through ligation-free assembly of vector components with oligonucleotide linkers, BioTechniques, 2008, 44: 924-926.

* cited by examiner

*Primary Examiner* — Li Zheng
(74) *Attorney, Agent, or Firm* — James E. Davis; Thomas Kelley

(57) ABSTRACT

The present invention provides methods for assembling DNA molecules in a predetermined order to produce a DNA construct useful in *Agrobacterium* mediated transformation in plants. The method employs ligation independent cloning of separate DNA elements where one of the DNA elements contains T-DNA borders from *Agrobacterium tumefaciens*. The invention further provides methods for assembling a construct containing an inverted repeat. Using this approach, DNA constructs are constructed rapidly, efficiently and directionally.

1 Claim, 12 Drawing Sheets

1 2 3 4

5'NNNNNNNNNNNNNGATCTCTTGG 3'
3'NNNNNNNNNNNNN 5'

5' NNNNNNNNNNNNN 3'
CTAGAGAACCNNNNNNNNNNNNN 5'

Annealing

5'NNNNNNNNNNNNNGATCTCTTGGNNNNNNNNNNNNN 3'
3'NNNNNNNNNNNNNCTAGAGAACCNNNNNNNNNNNNN 5'

5' GCTATTGCACGATCTCTTGG 3'

7 8 9 10

5' NNNNNNNNNNNNN 3'
3' NNNNNNNNNNNNNCGATAACGTG 5'

5' NNNNNNNNNNNNN 3'
3' CTAGAGAACCNNNNNNNNNNNNN 5'

Bridge Annealing

5' NNNNNNNNNNNNNGCTATTGCACGATCTCTTGGNNNNNNNNNNNNN 3'
3' NNNNNNNNNNNNNCGATAACGTGCTAGAGAACCNNNNNNNNNNNNN 5'

FIG. 1b

SEQUENCE LISTING

```
<160> NUMBER OF SEQ ID NOS: 35

<210> SEQ ID NO 1
<211> LENGTH: 10289
<212> TYPE: DNA
<213> ORGANISM: Artificial Sequence
<220> FEATURE:
<221> NAME/KEY: misc_feature
<222> LOCATION: (1)..(10289)
<223> OTHER INFORMATION: Synthetic Backbone DNA molecule

<400> SEQUENCE: 1

cgcgccttaa ttaagcggcc gcatcgatcg tgaagtttct catctaagcc cccatttgga      60

cgtgaatgta gacacgtcga aataaagatt tccgaattag aataatttgt ttattgcttt     120

cgcctataaa tacgacggat cgtaatttgt cgttttatca aaatgtactt tcattttata     180

ataacgctgc ggacatctac atttttgaat tgaaaaaaaa ttggtaatta ctctttcttt     240

ttctccatat tgaccatcat actcattgct gatccatgta gatttcccgg acatgaagcc     300

atttacaatt gaatatatcc tgccgccgct gccgctttgc acccggtgga gcttgcatgt     360

tggtttctac gcagaactga gccggttagg cagataattt ccattgagaa ctgagccatg     420

tgcaccttcc ccccaacacg gtgagcgacg gggcaacgga gtgatccaca tgggactttt     480

cctagcttgg ctgccatttt tggggtgagg ccgttcgcgg ccgaggggcg cagcccctgg     540

ggggatggga ggcccgcgtt agcgggccgg gagggttcga gaagggggggg cacccccctt     600

cggcgtgcgc ggtcacgcgc acagggcgca gccctggtta aaaacaaggt ttataaatat     660

tggtttaaaa gcaggttaaa agacaggtta gcggtggccg aaaaacgggc ggaaaccctt     720

gcaaatgctg gattttctgc ctgtggacag cccctcaaat gtcaataggt gcgcccctca     780

tctgtcagca ctctgcccct caagtgtcaa ggatcgcgcc cctcatctgt cagtagtcgc     840

gcccctcaag tgtcaatacc gcagggcact tatccccagg cttgtccaca tcatctgtgg     900

gaaactcgcg taaaatcagg cgttttcgcc gatttgcgag gctggccagc tccacgtcgc     960

cggccgaaat cgagcctgcc cctcatctgt caacgccgcg ccgggtgagt cggcccctca    1020

agtgtcaacg tccgcccctc atctgtcagt gagggccaag ttttccgcga ggtatccaca    1080

acgccggcgg ccggccgcgg tgtctcgcac acggcttcga cggcgtttct ggcgcgtttg    1140

cagggccata gacggccgcc agcccagcgg cgagggcaac cagcccggtg agcgtcggaa    1200

agggtcgatc gaccgatgcc cttgagagcc ttcaacccag tcagctcctt ccggtgggcg    1260

cggggcatga ctatcgtcgc cgcacttatg actgtcttct ttatcatgca actcgtagga    1320

caggtgccgg cagcgctctg ggtcattttc ggcgaggacc gctttcgctg gagcgcgacg    1380

atgatcggcc tgtcgcttgc ggtattcgga atcttgcacg ccctcgctca agccttcgtc    1440

actggtcccg ccaccaaacg tttcggcgag aagcaggcca ttatcgccgg catggcggcc    1500
```

-continued

```
gacgcgctgg gctacgtctt gctggcgttc gcgacgcgag gctggatggc cttccccatt   1560
atgattcttc tcgcttccgg cggcatcggg atgcccgcgt tgcaggccat gctgtccagg   1620
caggtagatg acgaccatca gggacagctt caaggatcgc tcgcggctct taccagccta   1680
acttcgatca ttggaccgct gatcgtcacg gcgatttatg ccgcctcggc gagcacatgg   1740
aacgggttgg catggattgt aggcgccgcc ctataccttg tctgcctccc cgcgttgcgt   1800
cgcggtgcat ggagccgggc cacctcgacc tgaatggaag ccggcggcac ctcgctaacg   1860
gattcaccac tccaagaatt ggagccaatc aattcttgcg gagaactgtg aatgcgcaaa   1920
ccaacccttg gcagaacata tccatcgcgt ccgccatctc cagcagccgc acgcggcgca   1980
tctcgggcag cgttgggtcc tggccacggg tgcgcatgat cgtgctcctg tcgttgagga   2040
cccggctagg ctggcggggt tgccttactg gttagcagaa tgaatcaccg atacgcgagc   2100
gaacgtgaag cgactgctgc tgcaaaacgt ctgcgacctg agcaacaaca tgaatggtct   2160
tcggtttccg tgtttcgtaa agtctggaaa cgcggaagtc agcgccctgc accattatgt   2220
tccggatctg catcgcagga tgctgctggc taccctgtgg aacacctaca tctgtattaa   2280
cgaagcgctg gcattgaccc tgagtgattt ttctctggtc ccgccgcatc cataccgcca   2340
gttgtttacc ctcacaacgt tccagtaacc gggcatgttc atcatcagta acccgtatcg   2400
tgagcatcct ctctcgtttc atcggtatca ttacccccat gaacagaaat cccccttaca   2460
cggaggcatc agtgaccaaa caggaaaaaa ccgcccttaa catggcccgc tttatcagaa   2520
gccagacatt aacgcttctg gagaaactca acgagctgga cgcggatgaa caggcagaca   2580
tctgtgaatc gcttcacgac cacgctgatg agctttaccg cagctgcctc gcgcgtttcg   2640
gtgatgacgg tgaaaacctc tgacacatgc agctcccgga gacggtcaca gcttgtctgt   2700
aagcggatgc cgggagcaga caagcccgtc agggcgcgtc agcgggtgtt ggcgggtgtc   2760
ggggcgcagc catgacccag tcacgtagcg atagcggagt gtatactggc ttaactatgc   2820
ggcatcagag cagattgtac tgagagtgca ccatatgcgg tgtgaaatac cgcacagatg   2880
cgtaaggaga aaataccgca tcaggcgctc ttccgcttcc tcgctcactg actcgctgcg   2940
ctcggtcgtt cggctgcggc gagcggtatc agctcactca aaggcggtaa tacggttatc   3000
cacagaatca ggggataacg caggaaagaa catgtgagca aaaggccagc aaaaggccag   3060
gaaccgtaaa aaggccgcgt tgctggcgtt tttccatagg ctccgccccc ctgacgagca   3120
tcacaaaaat cgacgctcaa gtcagaggtg gcgaaacccg acaggactat aaagatacca   3180
ggcgtttccc cctggaagct ccctcgtgcg ctctcctgtt ccgaccctgc cgcttaccgg   3240
atacctgtcc gcctttctcc cttcgggaag cgtggcgctt tctcatagct cacgctgtag   3300
gtatctcagt tcggtgtagg tcgttcgctc caagctgggc tgtgtgcacg aaccccccgt   3360
tcagcccgac cgctgcgcct tatccggtaa ctatcgtctt gagtccaacc cggtaagaca   3420
cgacttatcg ccactggcag cagccactgg taacaggatt agcagagcga ggtatgtagg   3480
cggtgctaca gagttcttga agtggtggcc taactacggc tacactagaa ggacagtatt   3540
tggtatctgc gctctgctga agccagttac cttcggaaaa agagttggta gctcttgatc   3600
cggcaaacaa accaccgctg gtagcggtgg tttttttgtt tgcaagcagc agattacgcg   3660
cagaaaaaaa ggatctcaag aagatccttt gatcttttct acggggtctg acgctcagtg   3720
gaacgaaaac tcacgttaag ggattttggt catgagatta tcaaaaagga tcttcaccta   3780
gatcctttta aattaaaaat gaagttttaa atcaatctaa agtatatatg agtaaacttg   3840
gtctgacagt taccaatgct taatcagtga ggcacctatc tcagcgatct gtctatttcg   3900
```

-continued

```
ttcatccata gttgcctgac tccccgtcgt gtagataact acgatacggg agggcttacc   3960
atctggcccc agtgctgcaa tgataccgcg agacccacgc tcaccggctc cagatttatc   4020
agcaataaac cagccagccg gaagggccga gcgcagaagt ggtcctgcaa ctttatccgc   4080
ctccatccag tctattaatt gttgccggga agctagagta agtagttcgc cagttaatag   4140
tttgcgcaac gttgttgcca ttgctgcagg tcgggagcac aggatgacgc ctaacaattc   4200
attcaagccg acaccgcttc gcggcgcggc ttaattcagg agttaaacat catgagggaa   4260
gcggtgatcg ccgaagtatc gactcaacta tcagaggtag ttggcgtcat cgagcgccat   4320
ctcgaaccga cgttgctggc cgtacatttg tacggctccg cagtggatgg cggcctgaag   4380
ccacacagtg atattgattt gctggttacg gtgaccgtaa ggcttgatga aacaacgcgg   4440
cgagctttga tcaacgacct tttggaaact tcggcttccc ctggagagag cgagattctc   4500
cgcgctgtag aagtcaccat tgttgtgcac gacgacatca ttccgtggcg ttatccagct   4560
aagcgcgaac tgcaatttgg agaatggcag cgcaatgaca ttcttgcagg tatcttcgag   4620
ccagccacga tcgacattga tctggctatc ttgctgacaa aagcaagaga acatagcgtt   4680
gccttggtag gtccagcggc ggaggaactc tttgatccgg ttcctgaaca ggatctattt   4740
gaggcgctaa atgaaacctt aacgctatgg aactcgccgc ccgactgggc tggcgatgag   4800
cgaaatgtag tgcttacgtt gtcccgcatt tggtacagcg cagtaaccgg caaaatcgcg   4860
ccgaaggatg tcgctgccga ctgggcaatg gagcgcctgc cggcccagta tcagcccgtc   4920
atacttgaag ctaggcaggc ttatcttgga caagaagatc gcttggcctc gcgcgcagat   4980
cagttggaag aatttgttca ctacgtgaaa ggcgagatca ccaaggtagt cggcaaataa   5040
tgtctaacaa ttcgttcaag ccgacgccgc ttcgcggcgc ggcttaactc aagcgttaga   5100
tgctgcaggc atcgtggtgt cacgctcgtc gtttggtatg gcttcattca gctccggttc   5160
ccaacgatca aggcgagtta catgatcccc catgttgtgc aaaaaagcgg ttagctcctt   5220
cggtcctccg atcgaggatt tttcggcgct gcgctacgtc cgcgaccgcg ttgagggatc   5280
aagccacagc agcccactcg accttctagc cgacccagac gagccaaggg atctttttgg   5340
aatgctgctc cgtcgtcagg ctttccgacg tttgggtggt tgaacagaag tcattatcgc   5400
acggaatgcc aagcactccc gaggggaacc ctgtggttgg catgcacata caaatggacg   5460
aacggataaa ccttttcacg ccctttttaaa tatccgatta ttctaataaa cgctcttttc   5520
tcttaggttt acccgccaat atatcctgtc aaacactgat agtttaaact gaaggcggga   5580
aacgacaatc tggcgcgcct gcggccgcct cgaggtcatt catatgcttg agaagagagt   5640
cgggatagtc caaaataaaa caaaggtaag attacctggt caaaagtgaa aacatcagtt   5700
aaaaggtggt ataaagtaaa atatcggtaa taaaaggtgg cccaaagtga aatttactct   5760
tttctactat tataaaaatt gaggatgttt ttgtcggtac tttgatacgt catttttgta   5820
tgaattggtt tttaagttta ttcgcttttg gaaatgcata tctgtatttg agtcgggttt   5880
taagttcgtt tgcttttgta aatacagagg gatttgtata agaaatatct ttaaaaaaac   5940
ccatatgcta atttgacata atttttgaga aaaatatata ttcaggcgaa ttctcacaat   6000
gaacaataat aagattaaaa tagctttccc ccgttgcagc gcatgggtat tttttctagt   6060
aaaaataaaa gataaactta gactcaaaac atttacaaaa acaaccccta aagttcctaa   6120
agcccaaagt gctatccacg atccatagca agcccagccc aacccaaccc aacccaaccc   6180
accccagtcc agccaactgg acaatagtct ccacaccccc ccactatcac cgtgagttgt   6240
ccgcacgcac cgcacgtctc gcagccaaaa aaaaaaaaag aaagaaaaaa aagaaaaaga   6300
```

-continued

```
aaaaacagca ggtgggtccg ggtcgtgggg gccggaaacg cgaggaggat cgcgagccag   6360
cgacgaggcc ggccctccct ccgcttccaa agaaacgccc cccatcgcca ctatatacat   6420
accccccct ctcctcccat ccccccaacc ctaccaccac caccaccacc acctccacct   6480
cctcccccct cgctgccgga cgacgagctc ctcccccctc cccctccgcc gccgccgcgc   6540
cggtaaccac cccgcccctc tcctctttct ttctccgttt tttttttccg tctcggtctc   6600
gatctttggc cttggtagtt tgggtgggcg agaggcggct tcgtgcgcgc ccagatcggt   6660
gcgcgggagg ggcgggatct cgcggctggg gctctcgccg gcgtggatcc ggcccggatc   6720
tcgcggggaa tggggctctc ggatgtagat ctgcgatccg ccgttgttgg gggagatgat   6780
ggggggttta aaatttccgc catgctaaac aagatcagga agaggggaaa agggcactat   6840
ggtttatatt tttatatatt tctgctgctt cgtcaggctt agatgtgcta gatctttctt   6900
tcttctttttt gtgggtagaa tttgaatccc tcagcattgt tcatcggtag tttttctttt   6960
catgatttgt gacaaatgca gcctcgtgcg gagctttttt gtaggtagac cgcggaccgg   7020
tcgcgcctca gcagtcgctg tcgttaaccc agcggtactc gctgaggcga tcgcgggccc   7080
ggtaccctgc aatgtgaccc tagacttgtc catcttctgg attggccaac ttaattaatg   7140
tatgaaataa aaggatgcac acatagtgac atgctaatca ctataatgtg ggcatcaaag   7200
ttgtgtgtta tgtgtaatta ctaattatct gaataagaga aagagatcat ccatatttct   7260
tatcctaaat gaatgtcacg tgtctttata attctttgat gaaccagatg cattttatta   7320
accaattcca tatacatata aatattaatc atatataatt aatatcaatt gggttagcaa   7380
aacaaatcta gtctaggtgt gttttgctaa ttattgggggg atagtgcaaa aagaaatcta   7440
cgttctcaat aattcagata gaaaacttaa taaagtgaga taatttacat agattgcttt   7500
tatcctttga tatatgtgaa accatgcatg atataaggaa aatagataga gaaataattt   7560
tttacatcgt tgaatatgta aacaatttaa ttcaagaagc taggaatata aatattgagg   7620
agtttatgat tattattatt attttgatgt tcaatgaagt ttttttaat ttcatatgaa   7680
gtatacaaaa attcttcata gatttttgtt tctatgccgt agttatcttt aatatatttg   7740
tggttgaaga aatttattgc tagaaacgaa tggattgtca atttttttt aaagcaaata   7800
tatatgaaat tatactgtat attattttag tcatgattaa aatgtggcct taattgaatc   7860
atctttctca ttcatttttt caaaagcata tcaggatgat tgatatttat ctattttaaa   7920
aattaattta agggttcaaa ttaaatttaa cttaaaagtg tcctaaccgt agttaaaggt   7980
ttactttaaa aaaatactat gaaaaatcta atcttctatg aatcgacctg caggatttaa   8040
atccatcgtt ctggggccta acgggccaag ctttccgatc ctacctgtca cttcatcaaa   8100
aggacagtag aaaaggaagg tggcacctac aaatgccatc attgcgataa aggaaaggct   8160
atcattcaag atgcctctgc cgacagtggt cccaaagatg gacccccacc cacgaggagc   8220
atcgtggaaa aagaagacgt tccaaccacg tcttcaaagc aagtggattg atgtgatact   8280
tccactgacg taagggatga cgcacaatcc cactatcctt cgcaagaccc ttcctctata   8340
taaggaagtt catttcattt ggagaggaca cgctgaaatc accagtctct ctctacaaga   8400
tcggggatct ctagctagac gatcgtttcg catgattgaa caagatggat tgcacgcagg   8460
ttctccggcc gcttgggtgg agaggctatt cggctatgac tgggcacaac agacaatcgg   8520
ctgctctgat gccgccgtgt tccggctgtc agcgcagggg cgcccggttc tttttgtcaa   8580
gaccgacctg tccggtgccc tgaatgaact gcaggacgag gcagcgcggc tatcgtggct   8640
ggccacgacg ggcgttcctt gcgcagctgt gctcgacgtt gtcactgaag cgggaaggga   8700
```

-continued

```
ctggctgcta ttgggcgaag tgccggggca ggatctcctg tcatctcacc ttgctcctgc   8760

cgagaaagta tccatcatgg ctgatgcaat gcggcggctg catacgcttg atccggctac   8820

ctgcccattc gaccaccaag cgaaacatcg catcgagcga gcacgtactc ggatggaagc   8880

cggtcttgtc gatcaggatg atctggacga agagcatcag gggctcgcgc cagccgaact   8940

gttcgccagg ctcaaggcgc gcatgcccga cggcgaggat ctcgtcgtga cccatggcga   9000

tgcctgcttg ccgaatatca tggtggaaaa tggccgcttt tctggattca tcgactgtgg   9060

ccggctgggt gtggcggacc gctatcagga catagcgttg gctacccgtg atattgctga   9120

agagcttggc ggcgaatggg ctgaccgctt cctcgtgctt tacggtatcg ccgctcccga   9180

ttcgcagcgc atcgccttct atcgccttct tgacgagttc ttctgagcgg gactctgggg   9240

ttcgaagaat tcccgatcgt tcaaacattt ggcaataaag tttcttaaga ttgaatcctg   9300

ttgccggtct tgcgatgatt atcatataat ttctgttgaa ttacgttaag catgtaataa   9360

ttaacatgta atgcatgacg ttatttatga gatgggtttt tatgattaga gtcccgcaat   9420

tatacattta atacgcgata gaaaacaaaa tatagcgcgc aaactaggat aaattatcgc   9480

gcgcggtgtc atctatgtta ctagatcggg gatatcgcgt gtctttataa ttctttgatg   9540

aaccagatgc attttattaa ccaattccat atacatataa atattaatca tatataatta   9600

atatcaattg ggttagcaaa acaaatctag tctaggtgtg ttttgctaat tattgggga    9660

tagtgcaaaa agaaatctac gttctcaata attcagatag aaaacttaat aaagtgagat   9720

aatttacata gattgctttt atcctttgat atatgtgaaa ccatgcatga tataaggaaa   9780

atagatagag aaataatttt ttacatcgtt gaatatgtaa acaatttaat tcaagaagct   9840

aggaatataa atattgagga gtttatgatt attattatta ttttgatgtt caatgaagtt   9900

ttttttaatt tcatatgaag tatacaaaaa ttcttcatag atttttgttt ctatgccgta   9960

gttatcttta atatatttgt ggttgaagaa atttattgct agaaacgaat ggattgtcaa  10020

ttttttttta aagcaaatat atatgaaatt atactgtata ttattttagt catgattaaa  10080

atgtggcctt aattgaatca tctttctcat tcatttttc aaaagcatat caggatgatt   10140

gatatttatc tattttaaaa attaatttaa gggttcaaat taaatttaac ttaaaagtgt  10200

cctaaccgta gttaaaggtt tactttaaaa aaatactatg aaaaatctaa tcttctatga  10260

atcgaccgct gatcgatcgc ggccgctgg                                    10289
```

```
<210> SEQ ID NO 2
<211> LENGTH: 69
<212> TYPE: DNA
<213> ORGANISM: Artificial Sequence
<220> FEATURE:
<221> NAME/KEY: misc_feature
<222> LOCATION: (1)..(69)
<223> OTHER INFORMATION: Synthetic DNA adapter

<400> SEQUENCE: 2

ccggtcgcgc ctcagcagtc gctgtcgtta acccagcggt actcgctgag gcgatcgcgg     60

gcccggtac                                                             69
```

```
<210> SEQ ID NO 3
<211> LENGTH: 1708
<212> TYPE: DNA
<213> ORGANISM: Arabidopsis thaliana

<400> SEQUENCE: 3

atggcaatgg aggttgggga gatgtctcag ccggaggcga cggcgagtct tctctctctc     60
```

-continued

```
gcttccgcca ctcagcaacc gtacgtctcc gagctcctct ctttcactct tgatcgtctc    120

cacaaggaac cggagctgct tcgagtggat gcggagcgga ttcagaggca aatgcaagag    180

gtggctgttg gaaattaccg cgcgtttatc accgctgctg atgctttgct tgcgatccgt    240

caggaagttt cttccattga taagcatctc gagtctctga ttggcgaagt cccaaaacta    300

acgtctggtt gcactgaatt tatcgattct gctgagaata ttttggagaa gaggaagatg    360

aaccaagcat tgctggcaaa tcacagcact cttcttgact tgcttgagat tcctcagctt    420

atggacacat gcgtgaggaa tggaaatttt gatgaggctc ttgacctgga agcatttgta    480

tcgaaacttg ctaccctgca tcccaaattg ccagttatcc aagcacttgc agcggaggtt    540

agacaaacaa ctcagtcact tctctcacag cttctccaga aactacgctc aaatatacag    600

ttaccagaat gtctccgcat tattggatac ttacgccgaa taggtgtctt tggcgagtat    660

gaaatgcgat tacagttctt aagatgccga gaggcatggc tcactggaat tcttgaggat    720

ttagatcaga aaaatgccta tgagtattta aaaggcatga taaactgtca cagaatgcac    780

ctatttgacg tggttaacca atatcgagct atattttctg atgatacatc tgggagcgaa    840

gaaaattatg atggtggact tttgtttagc tgggccatgc atcaaataac atcacacctg    900

aagactctaa aaatcatgct tccaaagatt actgaaggag gatctctatc aaatattttg    960

gatcagtgca tgtactgtgc gatggggctt ggtggggttg ggctagactt ccggggtctg   1020

cttcctccac tttttgaaga ggcggttcta aacttattct ccaagaacat gagtacagca   1080

gttgagaatt ttcagttagt tttggattca catcgatggg ttccattacc atctgttggc   1140

tttccttcaa gtggtattaa tgaagatagc aaggatgacg tcacacctcc atcatacttg   1200

atggagcacc cgccacttgc agttttcata aatggggtat cttctgcttt gaacgaatta   1260

cgtccttgtg ccccgctaag tctaaagaat gttgttgctc atgaactgat caaaggactc   1320

caggccgtgt ctgactcctt actaagatac aatacaactc ggatgcttcg actcagtgaa   1380

tccaatctat tcctttcact ttgccgagct tttgtcgagg tggtttttcc acattgcgcc   1440

acatgctttg gccgatgtta tccaggtggt gccacaatcg ttatggatgc caagagtgca   1500

tacgaaggtc tgggtcgcat cttagctgca tcgtcctctc aagaaccatc caacaaatct   1560

ccaaaggtca tcagcacgga cacaaaggat gcatcagaga atggtgtagc ctcccaacct   1620

gaagaaaaac aagccgagaa tccaaacgcg aaagaagaag ataacagtcc cattcctttg   1680

cagactcctg agataacacc cgagtctt                                      1708
```

<210> SEQ ID NO 4
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: Fully synthetic DNA primer molecule

<400> SEQUENCE: 4

```
gcagtcgctg tcgttaccat ggcaatggag gttgggg                              37
```

<210> SEQ ID NO 5
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: Fully synthetic DNA primer molecule

<400> SEQUENCE: 5
gcgagtaccg ctgggttcta agactcgggt gttatctcag gagtc 45

<210> SEQ ID NO 6
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Fully synthetic DNA primer molecule where u = uradine

<400> SEQUENCE: 6
gcagucgctg ucgtuaccat g 21

<210> SEQ ID NO 7
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Fully synthetic DNA primer molecule where u = uradine

<400> SEQUENCE: 7
gcgaguaccg cugggtucta 20

<210> SEQ ID NO 8
<211> LENGTH: 12001
<212> TYPE: DNA
<213> ORGANISM: Artificial Sequence
<220> FEATURE:
<221> NAME/KEY: misc_feature
<222> LOCATION: (1)..(12001)
<223> OTHER INFORMATION: Synthetic DNA plasmid molecule

<400> SEQUENCE: 8
tgaggcgatc gcgggcccgg taccctgcaa tgtgacccta gacttgtcca tcttctggat 60
tggccaactt aattaatgta tgaaataaaa ggatgcacac atagtgacat gctaatcact 120
ataatgtggg catcaaagtt gtgtgttatg tgtaattact aattatctga ataagagaaa 180
gagatcatcc atatttctta tcctaaatga atgtcacgtg tctttataat tctttgatga 240
accagatgca ttttattaac caattccata tacatataaa tattaatcat atataattaa 300
tatcaattgg gttagcaaaa caaatctagt ctaggtgtgt tttgctaatt attgggggat 360
agtgcaaaaa gaaatctacg ttctcaataa ttcagataga aaacttaata aagtgagata 420
atttacatag attgctttta tcctttgata tatgtgaaac catgcatgat ataaggaaaa 480
tagatagaga aataattttt tacatcgttg aatatgtaaa caatttaatt caagaagcta 540
ggaatataaa tattgaggag tttatgatta ttattattat tttgatgttc aatgaagttt 600
tttttaattt catatgaagt atacaaaaat tcttcataga tttttgtttc tatgccgtag 660
ttatctttaa tatatttgtg gttgaagaaa tttattgcta gaaacgaatg gattgtcaat 720
ttttttttaa agcaaatata tatgaaatta tactgtatat tattttagtc atgattaaaa 780
tgtggcctta attgaatcat ctttctcatt catttttttca aaagcatatc aggatgattg 840
atatttatct attttaaaaa ttaatttaag ggttcaaatt aaatttaact taaaagtgtc 900
ctaaccgtag ttaaaggttt actttaaaaa aatactatga aaaatctaat cttctatgaa 960
tcgacctgca ggatttaaat ccatcgttct ggggcctaac gggccaagct ttccgatcct 1020

-continued

```
acctgtcact tcatcaaaag gacagtagaa aaggaaggtg gcacctacaa atgccatcat   1080
tgcgataaag gaaaggctat cattcaagat gcctctgccg acagtggtcc caaagatgga   1140
cccccaccca cgaggagcat cgtggaaaaa gaagacgttc caaccacgtc ttcaaagcaa   1200
gtggattgat gtgatacttc cactgacgta agggatgacg cacaatccca ctatccttcg   1260
caagaccctt cctctatata aggaagttca tttcatttgg agaggacacg ctgaaatcac   1320
cagtctctct ctacaagatc ggggatctct agctagacga tcgtttcgca tgattgaaca   1380
agatggattg cacgcaggtt ctccggccgc ttgggtggag aggctattcg gctatgactg   1440
ggcacaacag acaatcggct gctctgatgc cgccgtgttc cggctgtcag cgcaggggcg   1500
cccggttctt tttgtcaaga ccgacctgtc cggtgccctg aatgaactgc aggacgaggc   1560
agcgcggcta tcgtggctgg ccacgacggg cgttccttgc gcagctgtgc tcgacgttgt   1620
cactgaagcg ggaagggact ggctgctatt gggcgaagtg ccggggcagg atctcctgtc   1680
atctcacctt gctcctgccg agaaagtatc catcatggct gatgcaatgc ggcggctgca   1740
tacgcttgat ccggctacct gcccattcga ccaccaagcg aaacatcgca tcgagcgagc   1800
acgtactcgg atggaagccg gtcttgtcga tcaggatgat ctggacgaag agcatcaggg   1860
gctcgcgcca gccgaactgt tcgccaggct caaggcgcgc atgcccgacg gcgaggatct   1920
cgtcgtgacc catggcgatg cctgcttgcc gaatatcatg gtggaaaatg gccgcttttc   1980
tggattcatc gactgtggcc ggctgggtgt ggcggaccgc tatcaggaca tagcgttggc   2040
tacccgtgat attgctgaag agcttggcgg cgaatgggct gaccgcttcc tcgtgcttta   2100
cggtatcgcc gctcccgatt cgcagcgcat cgccttctat cgccttcttg acgagttctt   2160
ctgagcggga ctctggggtt cgaagaattc ccgatcgttc aaacatttgg caataaagtt   2220
tcttaagatt gaatcctgtt gccggtcttg cgatgattat catataattt ctgttgaatt   2280
acgttaagca tgtaataatt aacatgtaat gcatgacgtt atttatgaga tgggttttta   2340
tgattagagt cccgcaatta tacatttaat acgcgataga aaacaaaata tagcgcgcaa   2400
actaggataa attatcgcgc gcggtgtcat ctatgttact agatcgggga tatcgcgtgt   2460
ctttataatt ctttgatgaa ccagatgcat tttattaacc aattccatat acatataaat   2520
attaatcata tataattaat atcaattggg ttagcaaaac aaatctagtc taggtgtgtt   2580
ttgctaatta ttgggggata gtgcaaaaag aaatctacgt tctcaataat tcagatagaa   2640
aacttaataa agtgagataa tttacataga ttgcttttat cctttgatat atgtgaaacc   2700
atgcatgata taaggaaaat agatagagaa ataatttttt acatcgttga atatgtaaac   2760
aatttaattc aagaagctag gaatataaat attgaggagt ttatgattat tattattatt   2820
ttgatgttca atgaagtttt ttttaatttc atatgaagta tacaaaaatt cttcatagat   2880
ttttgtttct atgccgtagt tatctttaat atatttgtgg ttgaagaaat ttattgctag   2940
aaacgaatgg attgtcaatt tttttttaaa gcaaatatat atgaaattat actgtatatt   3000
attttagtca tgattaaaat gtggccttaa ttgaatcatc tttctcattc atttttttcaa   3060
aagcatatca ggatgattga tatttatcta ttttaaaaat taatttaagg gttcaaatta   3120
aatttaactt aaaagtgtcc taaccgtagt taaaggttta ctttaaaaaa atactatgaa   3180
aaatctaatc ttctatgaat cgaccgctga tcgatcgcgg ccgctggcgc gccttaatta   3240
agcggccgca tcgatcgtga agtttctcat ctaagccccc atttggacgt gaatgtagac   3300
acgtcgaaat aaagatttcc gaattagaat aatttgttta ttgctttcgc ctataaatac   3360
gacggatcgt aatttgtcgt tttatcaaaa tgtactttca ttttataata acgctgcgga   3420
```

-continued

```
catctacatt tttgaattga aaaaaaattg gtaattactc tttctttttc tccatattga   3480
ccatcatact cattgctgat ccatgtagat ttcccggaca tgaagccatt tacaattgaa   3540
tatatcctgc cgccgctgcc gctttgcacc cggtggagct tgcatgttgg tttctacgca   3600
gaactgagcc ggttaggcag ataatttcca ttgagaactg agccatgtgc accttccccc   3660
caacacggtg agcgacgggg caacggagtg atccacatgg gacttttcct agcttggctg   3720
ccatttttgg ggtgaggccg ttcgcggccg aggggcgcag cccctggggg gatgggaggc   3780
ccgcgttagc gggccgggag ggttcgagaa ggggggcac cccccttcgg cgtgcgcggt   3840
cacgcgcaca gggcgcagcc ctggttaaaa acaaggttta taaatattgg tttaaaagca   3900
ggttaaaaga caggttagcg gtggccgaaa aacgggcgga aacccttgca aatgctggat   3960
tttctgcctg tggacagccc ctcaaatgtc aataggtgcg cccctcatct gtcagcactc   4020
tgcccctcaa gtgtcaagga tcgcgcccct catctgtcag tagtcgcgcc cctcaagtgt   4080
caataccgca gggcacttat ccccaggctt gtccacatca tctgtgggaa actcgcgtaa   4140
aatcaggcgt tttcgccgat ttgcgaggct ggccagctcc acgtcgccgg ccgaaatcga   4200
gcctgcccct catctgtcaa cgccgcgccg ggtgagtcgg cccctcaagt gtcaacgtcc   4260
gcccctcatc tgtcagtgag ggccaagttt tccgcgaggt atccacaacg ccggcggccg   4320
gccgcggtgt ctcgcacacg gcttcgacgg cgtttctggc gcgtttgcag ggccatagac   4380
ggccgccagc ccagcggcga gggcaaccag cccggtgagc gtcggaaagg gtcgatcgac   4440
cgatgccctt gagagccttc aacccagtca gctccttccg gtgggcgcgg ggcatgacta   4500
tcgtcgccgc acttatgact gtcttcttta tcatgcaact cgtaggacag gtgccggcag   4560
cgctctgggt cattttcggc gaggaccgct ttcgctggag cgcgacgatg atcggcctgt   4620
cgcttgcggt attcggaatc ttgcacgccc tcgctcaagc cttcgtcact ggtcccgcca   4680
ccaaacgttt cggcgagaag caggccatta tcgccggcat ggcggccgac gcgctgggct   4740
acgtcttgct ggcgttcgcg acgcgaggct ggatggcctt ccccattatg attcttctcg   4800
cttccggcgg catcgggatg cccgcgttgc aggccatgct gtccaggcag gtagatgacg   4860
accatcaggg acagcttcaa ggatcgctcg cggctcttac cagcctaact tcgatcattg   4920
gaccgctgat cgtcacggcg atttatgccg cctcggcgag cacatggaac gggttggcat   4980
ggattgtagg cgccgcccta taccttgtct gcctccccgc gttgcgtcgc ggtgcatgga   5040
gccgggccac ctcgacctga atggaagccg gcggcacctc gctaacggat tcaccactcc   5100
aagaattgga gccaatcaat tcttgcggag aactgtgaat gcgcaaacca acccttggca   5160
gaacatatcc atcgcgtccg ccatctccag cagccgcacg cggcgcatct cgggcagcgt   5220
tgggtcctgg ccacgggtgc gcatgatcgt gctcctgtcg ttgaggaccc ggctaggctg   5280
gcggggttgc cttactggtt agcagaatga atcaccgata cgcgagcgaa cgtgaagcga   5340
ctgctgctgc aaaacgtctg cgacctgagc aacaacatga atggtcttcg gtttccgtgt   5400
ttcgtaaagt ctggaaacgc ggaagtcagc gccctgcacc attatgttcc ggatctgcat   5460
cgcaggatgc tgctggctac cctgtggaac acctacatct gtattaacga agcgctggca   5520
ttgaccctga gtgatttttc tctggtcccg ccgcatccat accgccagtt gtttaccctc   5580
acaacgttcc agtaaccggg catgttcatc atcagtaacc cgtatcgtga gcatcctctc   5640
tcgtttcatc ggtatcatta cccccatgaa cagaaatccc ccttacacgg aggcatcagt   5700
gaccaaacag gaaaaaaccg cccttaacat ggcccgcttt atcagaagcc agacattaac   5760
gcttctggag aaactcaacg agctggacgc ggatgaacag gcagacatct gtgaatcgct   5820
```

-continued

```
tcacgaccac gctgatgagc tttaccgcag ctgcctcgcg cgtttcggtg atgacggtga   5880
aaacctctga cacatgcagc tcccggagac ggtcacagct tgtctgtaag cggatgccgg   5940
gagcagacaa gcccgtcagg gcgcgtcagc gggtgttggc gggtgtcggg gcgcagccat   6000
gacccagtca cgtagcgata gcggagtgta tactggctta actatgcggc atcagagcag   6060
attgtactga gagtgcacca tatgcggtgt gaaataccgc acagatgcgt aaggagaaaa   6120
taccgcatca ggcgctcttc cgcttcctcg ctcactgact cgctgcgctc ggtcgttcgg   6180
ctgcggcgag cggtatcagc tcactcaaag gcggtaatac ggttatccac agaatcaggg   6240
gataacgcag gaaagaacat gtgagcaaaa ggccagcaaa aggccaggaa ccgtaaaaag   6300
gccgcgttgc tggcgttttt ccataggctc cgcccccctg acgagcatca caaaaatcga   6360
cgctcaagtc agaggtggcg aaacccgaca ggactataaa gataccaggc gtttccccct   6420
ggaagctccc tcgtgcgctc tcctgttccg accctgccgc ttaccggata cctgtccgcc   6480
tttctccctt cgggaagcgt ggcgctttct catagctcac gctgtaggta tctcagttcg   6540
gtgtaggtcg ttcgctccaa gctgggctgt gtgcacgaac cccccgttca gcccgaccgc   6600
tgcgccttat ccggtaacta tcgtcttgag tccaacccgg taagacacga cttatcgcca   6660
ctggcagcag ccactggtaa caggattagc agagcgaggt atgtaggcgg tgctacagag   6720
ttcttgaagt ggtggcctaa ctacggctac actagaagga cagtatttgg tatctgcgct   6780
ctgctgaagc cagttacctt cggaaaaaga gttggtagct cttgatccgg caaacaaacc   6840
accgctggta gcggtggttt ttttgtttgc aagcagcaga ttacgcgcag aaaaaaagga   6900
tctcaagaag atcctttgat cttttctacg gggtctgacg ctcagtggaa cgaaaactca   6960
cgttaaggga ttttggtcat gagattatca aaaaggatct tcacctagat ccttttaaat   7020
taaaaatgaa gttttaaatc aatctaaagt atatatgagt aaacttggtc tgacagttac   7080
caatgcttaa tcagtgaggc acctatctca gcgatctgtc tatttcgttc atccatagtt   7140
gcctgactcc ccgtcgtgta gataactacg atacgggagg gcttaccatc tggccccagt   7200
gctgcaatga taccgcgaga cccacgctca ccggctccag atttatcagc aataaaccag   7260
ccagccggaa gggccgagcg cagaagtggt cctgcaactt tatccgcctc catccagtct   7320
attaattgtt gccgggaagc tagagtaagt agttcgccag ttaatagttt gcgcaacgtt   7380
gttgccattg ctgcaggtcg ggagcacagg atgacgccta acaattcatt caagccgaca   7440
ccgcttcgcg gcgcggctta attcaggagt taaacatcat gagggaagcg gtgatcgccg   7500
aagtatcgac tcaactatca gaggtagttg gcgtcatcga gcgccatctc gaaccgacgt   7560
tgctggccgt acatttgtac ggctccgcag tggatggcgg cctgaagcca cacagtgata   7620
ttgatttgct ggttacggtg accgtaaggc ttgatgaaac aacgcggcga gctttgatca   7680
acgacctttt ggaaacttcg gcttcccctg gagagagcga gattctccgc gctgtagaag   7740
tcaccattgt tgtgcacgac gacatcattc cgtggcgtta tccagctaag cgcgaactgc   7800
aatttggaga atggcagcgc aatgacattc ttgcaggtat cttcgagcca gccacgatcg   7860
acattgatct ggctatcttg ctgacaaaag caagagaaca tagcgttgcc ttggtaggtc   7920
cagcggcgga ggaactcttt gatccggttc ctgaacagga tctatttgag gcgctaaatg   7980
aaaccttaac gctatggaac tcgccgcccg actgggctgg cgatgagcga aatgtagtgc   8040
ttacgttgtc ccgcatttgg tacagcgcag taaccggcaa aatcgcgccg aaggatgtcg   8100
ctgccgactg ggcaatggag cgcctgccgg cccagtatca gcccgtcata cttgaagcta   8160
ggcaggctta tcttggacaa gaagatcgct tggcctcgcg cgcagatcag ttggaagaat   8220
```

-continued

```
ttgttcacta cgtgaaaggc gagatcacca aggtagtcgg caaataatgt ctaacaattc   8280
gttcaagccg acgccgcttc gcggcgcggc ttaactcaag cgttagatgc tgcaggcatc   8340
gtggtgtcac gctcgtcgtt tggtatggct tcattcagct ccggttccca acgatcaagg   8400
cgagttacat gatcccccat gttgtgcaaa aaagcggtta gctccttcgg tcctccgatc   8460
gaggattttt cggcgctgcg ctacgtccgc gaccgcgttg agggatcaag ccacagcagc   8520
ccactcgacc ttctagccga cccagacgag ccaagggatc tttttggaat gctgctccgt   8580
cgtcaggctt tccgacgttt gggtggttga acagaagtca ttatcgcacg gaatgccaag   8640
cactcccgag gggaaccctg tggttggcat gcacatacaa atggacgaac ggataaacct   8700
tttcacgccc ttttaaatat ccgattattc taataaacgc tcttttctct taggtttacc   8760
cgccaatata tcctgtcaaa cactgatagt ttaaactgaa ggcgggaaac gacaatctgg   8820
cgcgcctgcg gccgcctcga ggtcattcat atgcttgaga agagagtcgg gatagtccaa   8880
aataaaacaa aggtaagatt acctggtcaa aagtgaaaac atcagttaaa aggtggtata   8940
aagtaaaata tcggtaataa aaggtggccc aaagtgaaat ttactctttt ctactattat   9000
aaaaattgag gatgtttttg tcggtacttt gatacgtcat tttgtatga attggttttt   9060
aagtttattc gcttttggaa atgcatatct gtatttgagt cgggttttaa gttcgtttgc   9120
ttttgtaaat acagagggat ttgtataaga aatatcttta aaaaaaccca tatgctaatt   9180
tgacataatt tttgagaaaa atatatattc aggcgaattc tcacaatgaa caataataag   9240
attaaaatag ctttcccccg ttgcagcgca tgggtatttt ttctagtaaa aataaaagat   9300
aaacttagac tcaaaacatt tacaaaaaca acccctaaag ttcctaaagc ccaaagtgct   9360
atccacgatc catagcaagc ccagcccaac ccaacccaac ccaacccacc ccagtccagc   9420
caactggaca atagtctcca caccccccca ctatcaccgt gagttgtccg cacgcaccgc   9480
acgtctcgca gccaaaaaaa aaaaaagaaa gaaaaaaaag aaaaagaaaa aacagcaggt   9540
gggtccgggt cgtgggggcc ggaaacgcga ggaggatcgc gagccagcga cgaggccggc   9600
cctccctccg cttccaaaga aacgcccccc atcgccacta tatacatacc ccccctctc   9660
ctcccatccc cccaacccta ccaccaccac caccaccacc tccacctcct cccccctcgc   9720
tgccggacga cgagctcctc ccccctcccc ctccgccgcc gccgcgccgg taaccacccc   9780
gcccctctcc tctttctttc tccgtttttt ttttccgtct cggtctcgat ctttggcctt   9840
ggtagtttgg gtgggcgaga ggcggcttcg tgcgcgccca gatcggtgcg cgggaggggc   9900
gggatctcgc ggctggggct ctcgccggcg tggatccggc ccggatctcg cggggaatgg   9960
ggctctcgga tgtagatctg cgatccgccg ttgttggggg agatgatggg gggtttaaaa  10020
tttccgccat gctaaacaag atcaggaaga ggggaaaagg gcactatggt ttatattttt  10080
atatatttct gctgcttcgt caggcttaga tgtgctagat ctttctttct tctttttgtg  10140
ggtagaattt gaatccctca gcattgttca tcggtagttt ttcttttcat gatttgtgac  10200
aaatgcagcc tcgtgcggag ctttttttgta ggtagaccgc ggaccggtcg cgcctcagca  10260
gtcgctgtcg ttaccatggc aatggaggtt ggggagatgt ctcagccgga ggcgacggcg  10320
agtcttctct ctctcgcttc cgccactcag caaccgtacg tctccgagct cctctctttc  10380
actcttgatc gtctccacaa ggaaccggag ctgcttcgag tggatgcgga gcggattcag  10440
aggcaaatgc aagaggtggc tgttggaaat taccgcgcgt ttatcaccgc tgctgatgct  10500
ttgcttgcga tccgtcagga agtttcttcc attgataagc atctcgagtc tctgattggc  10560
gaagtcccaa aactaacgtc tggttgcact gaatttatcg attctgctga gaatattttg  10620
```

```
gagaagagga agatgaacca agcattgctg gcaaatcaca gcactcttct tgacttgctt  10680
gagattcctc agcttatgga cacatgcgtg aggaatggaa attttgatga ggctcttgac  10740
ctggaagcat ttgtatcgaa acttgctacc ctgcatccca aattgccagt tatccaagca  10800
cttgcagcgg aggttagaca aacaactcag tcacttctct cacagcttct ccagaaacta  10860
cgctcaaata tacagttacc agaatgtctc cgcattattg gatacttacg ccgaataggt  10920
gtctttggcg agtatgaaat gcgattacag ttcttaagat gccgagaggc atggctcact  10980
ggaattcttg aggatttaga tcagaaaaat gcctatgagt atttaaaagg catgataaac  11040
tgtcacagaa tgcacctatt tgacgtggtt aaccaatatc gagctatatt ttctgatgat  11100
acatctggga gcgaagaaaa ttatgatggt ggacttttgt ttagctgggc catgcatcaa  11160
ataacatcac acctgaagac tctaaaaatc atgcttccaa agattactga aggaggatct  11220
ctatcaaata ttttggatca gtgcatgtac tgtgcgatgg ggcttggtgg ggttgggcta  11280
gacttccggg gtctgcttcc tccacttttt gaagaggcgg ttctaaactt attctccaag  11340
aacatgagta cagcagttga gaattttcag ttagttttgg attcacatcg atgggttcca  11400
ttaccatctg ttggctttcc ttcaagtggt attaatgaag atagcaagga tgacgtcaca  11460
cctccatcat acttgatgga gcacccgcca cttgcagttt tcataaatgg ggtatcttct  11520
gctttgaacg aattacgtcc ttgtgccccg ctaagtctaa agaatgttgt tgctcatgaa  11580
ctgatcaaag gactccaggc cgtgtctgac tccttactaa gatacaatac aactcggatg  11640
cttcgactca gtgaatccaa tctattcctt tcactttgcc gagcttttgt cgaggtggtt  11700
tttccacatt gcgccacatg ctttggccga tgttatccag gtggtgccac aatcgttatg  11760
gatgccaaga gtgcatacga aggtctgggt cgcatcttag ctgcatcgtc ctctcaagaa  11820
ccatccaaca aatctccaaa ggtcatcagc acggacacaa aggatgcatc agagaatggt  11880
gtagcctccc aacctgaaga aaaacaagcc gagaatccaa acgcgaaaga agaagataac  11940
agtcccattc ctttgcagac tcctgagata acacccgagt cttagaaccc agcggtactc  12000
g                                                                  12001

<210> SEQ ID NO 9
<211> LENGTH: 1409
<212> TYPE: DNA
<213> ORGANISM: Zea mays

<400> SEQUENCE: 9

ccgatcgatc gccacagcca acaccacccg ccgaggcgac gcgacagccg ccaggaggaa     60
ggaataaact cactgccagc cagtgaaggg ggagaagtgt actgctccgt cgaccagtgc    120
gcgcaccgcc cggcagggct gctcatctcg tcgacgacca gtggattaat cggcatggcg    180
gctctggcca cgtcgcagct cgtcgcaacg cccgccggcc tgggcgtccc ggacgcgtcc    240
acgttccgcc gcggcgccgc gcagggcctg agggggggccc gggcgtcggc ggcggcggac    300
acgctcagca tgcggaccag cgcgcgcgcg gcgcccaggc accagcagca ggcgcgccgc    360
gggggcaggt tcccgtcgct cgtcgtgtgc gccagcgccg gcatgaacgt cgtcttcgtc    420
ggcgccgaga tggcgccgtg gagcaagacc ggcggcctcg gcgacgtcct cggcggcctg    480
ccgccggcca tggccgcgaa cgggcaccgt gtcatggtcg tctctccccg ctacgaccag    540
tacaaggacg cctgggacac cagcgtcgtg tccgagatca agatgggaga cgggtacgag    600
acggtcaggt tcttccactg ctacaagcgc ggagtggacc gcgtgttcgt tgaccaccca    660
ctgttcctgg agagggtttg ggaaaagacc gaggagaaga tctacgggcc tgtcgctgga    720
```

```
acggactaca gggacaacca gctgcggttc agcctgctat gccaggcagc acttgaagct    780

ccaaggatcc tgagcctcaa caacaaccca tacttctccg gaccatacgg ggaggacgtc    840

gtgttcgtct gcaacgactg gcacaccggc cctctctcgt gctacctcaa gagcaactac    900

cagtcccacg gcatctacag ggacgcaaag accgctttct gcatccacaa catctcctac    960

cagggccggt tcgccttctc cgactacccg gagctgaacc tcccggagag attcaagtcg   1020

tccttcgatt tcatcgacgg ctacgagaag cccgtggaag gccggaagat caactggatg   1080

aaggccggga tcctcgaggc cgacagggtc ctcaccgtca gcccctacta cgccgaggag   1140

ctcatctccg gcatcgccag gggctgcgag ctcgacaaca tcatgcgcct caccggcatc   1200

accggcatcg tcaacggcat ggacgtcagc gagtgggacc ccagcaggga caagtacatc   1260

gccgtgaagt acgacgtgtc gacggccgtg gaggccaagg cgctgaacaa ggaggcgctg   1320

caggcggagg tcgggctccc ggtggaccgg aacatcccgc tggtggcgtt catcggcagg   1380

ctggaagagc agaagggccc cgacgtcat                                     1409
```

<210> SEQ ID NO 10
<211> LENGTH: 52
<212> TYPE: DNA
<213> ORGANISM: Artificial Sequence
<220> FEATURE:
<221> NAME/KEY: misc_feature
<222> LOCATION: (1)..(52)
<223> OTHER INFORMATION: Fully synthetic DNA primer molecule

<400> SEQUENCE: 10

```
aagtactgcg atcgcgttaa cgctagattc aagtcgtcct tcgatttcat cg             52
```

<210> SEQ ID NO 11
<211> LENGTH: 44
<212> TYPE: DNA
<213> ORGANISM: Artificial Sequence
<220> FEATURE:
<221> NAME/KEY: misc_feature
<222> LOCATION: (1)..(44)
<223> OTHER INFORMATION: Fully synthetic DNA primer molecule

<400> SEQUENCE: 11

```
gcagtcgctg tgcgatacca cgtcggggcc cttctgctct tcca                     44
```

<210> SEQ ID NO 12
<211> LENGTH: 51
<212> TYPE: DNA
<213> ORGANISM: Artificial Sequence
<220> FEATURE:
<221> NAME/KEY: misc_feature
<222> LOCATION: (1)..(51)
<223> OTHER INFORMATION: Fully synthetic DNA primer molecule

<400> SEQUENCE: 12

```
agcgttaacg cgatcgcagt acttgaagct ccaaggatcc tgagcctcaa c              51
```

<210> SEQ ID NO 13
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: Fully synthetic DNA primer molecule

<400> SEQUENCE: 13

```
gcgagtaccg ctggcgatct aacgtcgggg cccttctgct cttcc                    45
```

```
<210> SEQ ID NO 14
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Fully synthetic DNA primer molecule where
      u = uradine

<400> SEQUENCE: 14

aaguactgcg aucgcgtuaa cgcu                                              24

<210> SEQ ID NO 15
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Fully synthetic DNA primer molecule where
      u = uradine

<400> SEQUENCE: 15

gcagucgcug ugcgauacc                                                    19

<210> SEQ ID NO 16
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Fully synthetic DNA primer molecule where
      u = uradine

<400> SEQUENCE: 16

agcgtuaacg cgaucgcagu acuu                                              24

<210> SEQ ID NO 17
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Fully synthetic DNA primer molecule where
      u = uradine

<400> SEQUENCE: 17

gcgaguaccg cuggcgauct a                                                 21

<210> SEQ ID NO 18
<211> LENGTH: 11870
<212> TYPE: DNA
<213> ORGANISM: Artificial Sequence
<220> FEATURE:
<221> NAME/KEY: misc_feature
<222> LOCATION: (1)..(11870)
<223> OTHER INFORMATION: Synthetic DNA plasmid molecule

<400> SEQUENCE: 18

gtcccgcgtc aatattatta aaaaactcct acatttcttt ataatcaacc cgcactctta       60

taatctcttc tctactacta taataagaga gtttatgtac aaaataaggt gaaattatgt      120

ataagtgttc tggatattgg ttgttggctc catattcaca caacctaatc aatagaaaac      180

atatgtttta ttaaaacaaa atttatcata tatcatatat atatatatac atatatatat      240
```

-continued

```
atatatataa accgtagcaa tgcacgggca tataactagt gcaacttaat acatgtgtgt    300
attaagatga ataagagggt atccaaataa aaaacttgtt cgcttacgtc tggatcgaaa    360
ggggttggaa acgattaaat ctcttcctag tcaaaattga atagaaggag atttaatctc    420
tcccaatccc cttcgatcat ccaggtgcaa ccgtataagt cctaaagtgg tgaggaacac    480
gaaacaacca tgcattggca tgtaaagctc caagaatttg ttgtatcctt aacaactcac    540
agaacatcaa ccaaaattgc acgtcaaggg tattgggtaa gaaacaatca aacaaatcct    600
ctctgtgtgc aaagaaacac ggtgagtcat gccgagatca tactcatctg atatacatgc    660
ttacagctca caagacatta caaacaactc atattgcatt acaaagatcg tttcatgaaa    720
aataaaatag gccggacagg acaaaaatcc ttgacgtgta aagtaaattt acaacaaaaa    780
aaaagccata tgtcaagcta aatctaattc gttttacgta gatcaacaac ctgtagaagg    840
caacaaaact gagccacgca gaagtacaga atgattccag atgaaccatc gacgtgctac    900
gtaaagagag tgacgagtca tatacatttg gcaagaaacc atgaagctgc ctacagccgt    960
ctcggtggca taagaacaca agaaattgtg ttaattaatc aaagctataa ataacgctcg   1020
catgcctgtg cacttctcca tcaccaccac tgggtcttca gaccattagc tttatctact   1080
ccagagcgca gaagaacccg ggcccaccgt cttcggtacg cgctcactcc gccctctgcc   1140
tttgttactg ccacgtttct ctgaatgctc tcttgtgtgg tgattgctga gagtggttta   1200
gctggatcta gaattacact ctgaaatcgt gttctgcctg tgctgattac ttgccgtcct   1260
ttgtagcagc aaaatatagg gacatggtag tacgaaacga agatagaacc tacacagcaa   1320
tacgagaaat gtgtaatttg gtgcttagcg gtatttattt aagcacatgt tggtgttata   1380
gggcacttgg attcagaagt ttgctgttaa tttaggcaca ggcttcatac tacatgggtc   1440
aatagtatag ggattcatat tataggcgat actataataa tttgttcgtc tgcagagctt   1500
attatttgcc aaaattagat attcctattc tgtttttgtt tgtgtgctgt taaattgtta   1560
acgcctgaag gaataaatat aaatgacgaa attttgatgt ttatctctgc tcctttattg   1620
tgaccataag tcaagatcag atgcacttgt tttaaatatt gttgtctgaa gaaataagta   1680
ctgacagtat tttgatgcat tgatctgctt gtttgttgta acaaaattta aaaataaaga   1740
gtttcctttt tgttgctctc cttacctcct gatggtatct agtatctacc aactgacact   1800
atattgcttc tctttacata cgtatcttgc tcgatgcctt ctccctagtg ttgaccagtg   1860
ttactcacat agtctttgct catttcattg taatgcagat accaagcggg agctcgacgt   1920
ccctcagcag tcgctgtgcg ataccacgtc ggggcccttc tgctcttcca gcctgccgat   1980
gaacgccacc agcgggatgt tccggtccac cgggagcccg acctccgcct gcagcgcctc   2040
cttgttcagc gccttggcct ccacggccgt cgacacgtcg tacttcacgg cgatgtactt   2100
gtccctgctg gggtcccact cgctgacgtc catgccgttg acgatgccgg tgatgccggt   2160
gaggcgcatg atgttgtcga gctcgcagcc cctggcgatg ccggagatga gctcctcggc   2220
gtagtagggg ctgacggtga ggaccctgtc ggcctcgagg atcccggcct tcatccagtt   2280
gatcttccgg ccttccacgg gcttctcgta gccgtcgatg aaatcgaagg acgacttgaa   2340
tctctccggg aggttcagct ccgggtagtc ggagaaggcg aaccggccct ggtaggagat   2400
gttgtggatg cagaaagcgg tctttgcgtc cctgtagatg ccgtgggact ggtagttgct   2460
cttgaggtag cacgagagag ggccggtgtg ccagtcgttg cagacgaaca cgacgtcctc   2520
cccgtatggt ccggagaagt atgggttgtt gttgaggctc aggatccttg gagcttcaag   2580
tactgcgatc gcgttaacgc tagattcaag tcgtccttcg atttcatcga cggctacgag   2640
```

-continued

```
aagcccgtgg aaggccggaa gatcaactgg atgaaggccg ggatcctcga ggccgacagg   2700
gtcctcaccg tcagccccta ctacgccgag gagctcatct ccggcatcgc caggggctgc   2760
gagctcgaca acatcatgcg cctcaccggc atcaccggca tcgtcaacgg catggacgtc   2820
agcgagtggg accccagcag ggacaagtac atcgccgtga agtacgacgt gtcgacggcc   2880
gtggaggcca aggcgctgaa caaggaggcg ctgcaggcgg aggtcgggct cccggtggac   2940
cggaacatcc cgctggtggc gttcatcggc aggctggaag agcagaaggg ccccgacgtt   3000
agatcgccag cggtactcgc tgaggcctag gcgcggatcc cccaccctgc aatgtgaccc   3060
tagacttgtc catcttctgg attggccaac ttaattaatg tatgaaataa aaggatgcac   3120
acatagtgac atgctaatca ctataatgtg ggcatcaaag ttgtgtgtta tgtgtaatta   3180
ctaattatct gaataagaga aagagatcat ccatatttct tatcctaaat gaatgtcacg   3240
tgtctttata attctttgat gaaccagatg cattttatta accaattcca tatacatata   3300
aatattaatc atatataatt aatatcaatt gggttagcaa aacaaatcta gtctaggtgt   3360
gttttgctaa ttattggggg atagtgcaaa aagaaatcta cgttctcaat aattcagata   3420
gaaaacttaa taaagtgaga taatttacat agattgcttt tatcctttga tatatgtgaa   3480
accatgcatg atataaggaa aatagataga gaaataattt tttacatcgt tgaatatgta   3540
aacaatttaa ttcaagaagc taggaatata aatattgagg agtttatgat tattattatt   3600
attttgatgt tcaatgaagt ttttttaat ttcatatgaa gtatacaaaa attcttcata   3660
gatttttgtt tctatgccgt agttatcttt aatatatttg tggttgaaga aatttattgc   3720
tagaaacgaa tggattgtca attttttttt aaagcaaata tatatgaaat tatactgtat   3780
attattttag tcatgattaa aatgtggcct taattgaatc atctttctca ttcatttttt   3840
caaaagcata tcaggatgat tgatatttat ctattttaaa aattaattta agggttcaaa   3900
ttaaatttaa cttaaaagtg tcctaaccgt agttaaaggt ttactttaaa aaaatactat   3960
gaaaaatcta atcttctatg aatcgaccgg atttaaatcc atcgttctgg ggcctaacgg   4020
gccaagcttt ccgatcctac ctgtcacttc atcaaaagga cagtagaaaa ggaaggtggc   4080
acctacaaat gccatcattg cgataaagga aaggctatca ttcaagatgc ctctgccgac   4140
agtggtccca aagatggacc cccacccacg aggagcatcg tggaaaaaga agacgttcca   4200
accacgtctt caaagcaagt ggattgatgt gatacttcca ctgacgtaag ggatgacgca   4260
caatcccact atccttcgca agacccttcc tctatataag gaagttcatt tcatttggag   4320
aggacacgct gaaatcacca gtctctctct acaagatcgg ggatctctag ctagacgatc   4380
gtttcgcatg attgaacaag atggattgca cgcaggttct ccggccgctt gggtggagag   4440
gctattcggc tatgacattc ggctatgact gggcacaaca gacaatcggc tgctctgatg   4500
ccgccgtgtt ccggctgtca gcgcaggggc gcccggttct ttttgtcaag accgacctgt   4560
ccggtgccct gaatgaactg caggacgagg cagcgcggct atcgtggctg gccacgacgg   4620
gcgttccttg cgcagctgtg ctcgacgttg tcactgaagc gggaagggac tggctgctat   4680
tgggcgaagt gccggggcag gatctcctgt catctcacct tgctcctgcc gagaaagtat   4740
ccatcatggc tgatgcaatg cggcggctgc atacgcttga tccggctacc tgcccattcg   4800
accaccaagc gaaacatcgc atcgagcgag cacgtactcg gatggaagcc ggtcttgtcg   4860
atcaggatga tctggacgaa gagcatcagg ggctcgcgcc agccgaactg ttcgccaggc   4920
tcaaggcgcg catgcccgac ggcgaggatc tcgtcgtgac ccatggcgat gcctgcttgc   4980
cgaatatcat ggtggaaaat ggccgctttt ctggattcat cgactgtggc cggctgggtg   5040
```

-continued

```
tggcggaccg ctatcaggac atagcgttgg ctacccgtga tattgctgaa gagcttggcg   5100
gcgaatgggc tgaccgcttc ctcgtgcttt acggtatcgc cgctcccgat tcgcagcgca   5160
tcgccttcta tcgccttctt gacgagttct tctgagcggg actctggggt tcgaagaatt   5220
cccgatcgtt caaacatttg gcaataaagt ttcttaagat tgaatcctgt tgccggtctt   5280
gcgatgatta tcatataatt tctgttgaat tacgttaagc atgtaataat taacatgtaa   5340
tgcatgacgt tatttatgag atgggttttt atgattagag tcccgcaatt atacatttaa   5400
tacgcgatag aaaacaaaat atagcgcgca aactaggata aattatcgcg cgcggtgtca   5460
tctatgttac tagatcgggg atatcgcgtg tctttataat tctttgatga accagatgca   5520
ttttattaac caattccata tacatataaa tattaatcat atataattaa tatcaattgg   5580
gttagcaaaa caaatctagt ctaggtgtgt tttgctaatt attgggggat agtgcaaaaa   5640
gaaatctacg ttctcaataa ttcagataga aaacttaata aagtgagata atttacatag   5700
attgctttta tcctttgata tatgtgaaac catgcatgat ataaggaaaa tagatagaga   5760
aataattttt tacatcgttg aatatgtaaa caatttaatt caagaagcta ggaatataaa   5820
tattgaggag tttatgatta ttattattat tttgatgttc aatgaagttt tttttaattt   5880
catatgaagt atacaaaaat tcttcataga tttttgtttc tatgccgtag ttatctttaa   5940
tatatttgtg gttgaagaaa tttattgcta gaaacgaatg gattgtcaat tttttttaa    6000
agcaaatata tatgaaatta tactgtatat tattttagtc atgattaaaa tgtggcctta   6060
attgaatcat ctttctcatt cattttttca aaagcatatc aggatgattg atatttatct   6120
attttaaaaa ttaatttaag ggttcaaatt aaatttaact taaaagtgtc ctaaccgtag   6180
ttaaaggttt actttaaaaa aatactatga aaaatctaat cttctatgaa tcgaccgctg   6240
atcgatcgcg gccgctggcg cgccttaatt aagcggccgc atcgatcgtg aagtttctca   6300
tctaagcccc catttggacg tgaatgtaga cacgtcgaaa taaagatttc cgaattagaa   6360
taatttgttt attgctttcg cctataaata cgacggatcg taatttgtcg ttttatcaaa   6420
atgtactttc attttataat aacgctgcgg acatctacat ttttgaattg aaaaaaaatt   6480
ggtaattact ctttcttttt ctccatattg accatcatac tcattgctga tccatgtaga   6540
tttcccggac atgaagccat ttacaattga atatatcctg ccgccgctgc cgctttgcac   6600
ccggtggagc ttgcatgttg gtttctacgc agaactgagc cggttaggca gataatttcc   6660
attgagaact gagccatgtg caccttcccc ccaacacggt gagcgacggg gcaacggagt   6720
gatccacatg ggacttttcc tagcttggct gccatttttg gggtgaggcc gttcgcggcc   6780
gaggggcgca gcccctgggg ggatgggagg cccgcgttag cgggccggga gggttcgaga   6840
agggggggca ccccccttcg gcgtgcgcgg tcacgcgcac agggcgcagc cctggttaaa   6900
aacaaggttt ataaatattg gtttaaaagc aggttaaaag acaggttagc ggtggccgaa   6960
aaacgggcgg aaacccttgc aaatgctgga ttttctgcct gtggacagcc cctcaaatgt   7020
caataggtgc gcccctcatc tgtcagcact ctgcccctca agtgtcaagg atcgcgcccc   7080
tcatctgtca gtagtcgcgc ccctcaagtg tcaataccgc agggcactta tccccaggct   7140
tgtccacatc atctgtggga aactcgcgta aaatcaggcg ttttcgccga tttgcgaggc   7200
tggccagctc cacgtcgccg gccgaaatcg agcctgcccc tcatctgtca acgccgcgcc   7260
gggtgagtcg gcccctcaag tgtcaacgtc cgcccctcat ctgtcagtga gggccaagtt   7320
ttccgcgagg tatccacaac gccggcggcc ggccgcggtg tctcgcacac ggcttcgacg   7380
gcgtttctgg cgcgtttgca gggccataga cggccgccag cccagcggcg agggcaacca   7440
```

-continued gcccggtgag cgtcggaaag ggtcgatcga ccgatgccct tgagagcctt caacccagtc 7500
agctccttcc ggtgggcgcg gggcatgact atcgtcgccg cacttatgac tgtcttcttt 7560
atcatgcaac tcgtaggaca ggtgccggca gcgctctggg tcattttcgg cgaggaccgc 7620
tttcgctgga gcgcgacgat gatcggcctg tcgcttgcgg tattcggaat cttgcacgcc 7680
ctcgctcaag ccttcgtcac tggtcccgcc accaaacgtt tcggcgagaa gcaggccatt 7740
atcgccggca tggcggccga cgcgctgggc tacgtcttgc tggcgttcgc gacgcgaggc 7800
tggatggcct tccccattat gattcttctc gcttccggcg gcatcgggat gcccgcgttg 7860
caggccatgc tgtccaggca ggtagatgac gaccatcagg gacagcttca aggatcgctc 7920
gcggctctta ccagcctaac ttcgatcatt ggaccgctga tcgtcacggc gatttatgcc 7980
gcctcggcga gcacatggaa cgggttggca tggattgtag gcgccgccct ataccttgtc 8040
tgcctccccg cgttgcgtcg cggtgcatgg agccgggcca cctcgacctg aatggaagcc 8100
ggcggcacct cgctaacgga ttcaccactc caagaattgg agccaatcaa ttcttgcgga 8160
gaactgtgaa tgcgcaaacc aacccttggc agaacatatc catcgcgtcc gccatctcca 8220
gcagccgcac gcggcgcatc tcgggcagcg ttgggtcctg gccacgggtg cgcatgatcg 8280
tgctcctgtc gttgaggacc cggctaggct ggcggggttg ccttactggt tagcagaatg 8340
aatcaccgat acgcgagcga acgtgaagcg actgctgctg caaaacgtct gcgacctgag 8400
caacaacatg aatggtcttc ggtttccgtg tttcgtaaag tctggaaacg cggaagtcag 8460
cgccctgcac cattatgttc cggatctgca tcgcaggatg ctgctggcta ccctgtggaa 8520
cacctacatc tgtattaacg aagcgctggc attgaccctg agtgattttt ctctggtccc 8580
gccgcatcca taccgccagt tgtttaccct cacaacgttc cagtaaccgg gcatgttcat 8640
catcagtaac ccgtatcgtg agcatcctct ctcgtttcat cggtatcatt acccccatga 8700
acagaaatcc cccttacacg gaggcatcag tgaccaaaca ggaaaaaacc gcccttaaca 8760
tggcccgctt tatcagaagc cagacattaa cgcttctgga gaaactcaac gagctggacg 8820
cggatgaaca ggcagacatc tgtgaatcgc ttcacgacca cgctgatgag ctttaccgca 8880
gctgcctcgc gcgtttcggt gatgacggtg aaaacctctg acacatgcag ctcccggaga 8940
cggtcacagc ttgtctgtaa gcggatgccg ggagcagaca agcccgtcag ggcgcgtcag 9000
cgggtgttgg cgggtgtcgg ggcgcagcca tgacccagtc acgtagcgat agcggagtgt 9060
atactggctt aactatgcgg catcagagca gattgtactg agagtgcacc atatgcggtg 9120
tgaaataccg cacagatgcg taaggagaaa ataccgcatc aggcgctctt ccgcttcctc 9180
gctcactgac tcgctgcgct cggtcgttcg gctgcggcga gcggtatcag ctcactcaaa 9240
ggcggtaata cggttatcca cagaatcagg ggataacgca ggaaagaaca tgtgagcaaa 9300
aggccagcaa aaggccagga accgtaaaaa ggccgcgttg ctggcgtttt tccataggct 9360
ccgcccccct gacgagcatc acaaaaatcg acgctcaagt cagaggtggc gaaacccgac 9420
aggactataa agataccagg cgtttccccc tggaagctcc ctcgtgcgct ctcctgttcc 9480
gaccctgccg cttaccggat acctgtccgc ctttctccct tcgggaagcg tggcgctttc 9540
tcatagctca cgctgtaggt atctcagttc ggtgtaggtc gttcgctcca agctgggctg 9600
tgtgcacgaa ccccccgttc agcccgaccg ctgcgcctta tccggtaact atcgtcttga 9660
gtccaacccg gtaagacacg acttatcgcc actggcagca gccactggta acaggattag 9720
cagagcgagg tatgtaggcg gtgctacaga gttcttgaag tggtggccta actacggcta 9780
cactagaagg acagtatttg gtatctgcgc tctgctgaag ccagttacct tcggaaaaag 9840

```
agttggtagc tcttgatccg gcaaacaaac caccgctggt agcggtggtt tttttgtttg   9900

caagcagcag attacgcgca gaaaaaaagg atctcaagaa gatcctttga tcttttctac   9960

ggggtctgac gctcagtgga acgaaaactc acgttaaggg attttggtca tgagattatc  10020

aaaaaggatc ttcacctaga tccttttaaa ttaaaaatga agttttaaat caatctaaag  10080

tatatatgag taaacttggt ctgacagtta ccaatgctta atcagtgagg cacctatctc  10140

agcgatctgt ctatttcgtt catccatagt tgcctgactc cccgtcgtgt agataactac  10200

gatacgggag ggcttaccat ctggccccag tgctgcaatg ataccgcgag acccacgctc  10260

accggctcca gatttatcag caataaacca gccagccgga agggccgagc gcagaagtgg  10320

tcctgcaact ttatccgcct ccatccagtc tattaattgt tgccgggaag ctagagtaag  10380

tagttcgcca gttaatagtt tgcgcaacgt tgttgccatt gctgcaggtc gggagcacag  10440

gatgacgcct aacaattcat tcaagccgac accgcttcgc ggcgcggctt aattcaggag  10500

ttaaacatca tgagggaagc ggtgatcgcc gaagtatcga ctcaactatc agaggtagtt  10560

ggcgtcatcg agcgccatct cgaaccgacg ttgctggccg tacatttgta cggctccgca  10620

gtggatggcg gcctgaagcc acacagtgat attgatttgc tggttacggt gaccgtaagg  10680

cttgatgaaa caacgcggcg agctttgatc aacgaccttt tggaaacttc ggcttcccct  10740

ggagagagcg agattctccg cgctgtagaa gtcaccattg ttgtgcacga cgacatcatt  10800

ccgtggcgtt atccagctaa gcgcgaactg caatttggag aatggcagcg caatgacatt  10860

cttgcaggta tcttcgagcc agccacgatc gacattgatc tggctatctt gctgacaaaa  10920

gcaagagaac atagcgttgc cttggtaggt ccagcggcgg aggaactctt tgatccggtt  10980

cctgaacagg atctatttga ggcgctaaat gaaaccttaa cgctatggaa ctcgccgccc  11040

gactgggctg gcgatgagcg aaatgtagtg cttacgttgt cccgcatttg gtacagcgca  11100

gtaaccggca aaatcgcgcc gaaggatgtc gctgccgact gggcaatgga gcgcctgccg  11160

gcccagtatc agcccgtcat acttgaagct aggcaggctt atcttggaca agaagatcgc  11220

ttggcctcgc gcgcagatca gttggaagaa tttgttcact acgtgaaagg cgagatcacc  11280

aaggtagtcg gcaaataatg tctaacaatt cgttcaagcc gacgccgctt cgcggcgcgg  11340

cttaactcaa gcgttagatg ctgcaggcat cgtggtgtca cgctcgtcgt ttggtatggc  11400

ttcattcagc tccggttccc aacgatcaag gcgagttaca tgatccccca tgttgtgcaa  11460

aaaagcggtt agctccttcg gtcctccgat cgaggatttt tcggcgctgc gctacgtccg  11520

cgaccgcgtt gagggatcaa gccacagcag cccactcgac cttctagccg acccagacga  11580

gccaagggat ctttttggaa tgctgctccg tcgtcaggct ttccgacgtt tgggtggttg  11640

aacagaagtc attatcgcac ggaatgccaa gcactcccga ggggaaccct gtggttggca  11700

tgcacataca aatggacgaa cggataaacc ttttcacgcc cttttaaata tccgattatt  11760

ctaataaacg ctcttttctc ttaggtttac ccgccaatat atcctgtcaa acactgatag  11820

tttaaactga aggcgggaaa cgacaatctg gcgcgccgct agcctgcagg             11870
```

<210> SEQ ID NO 19
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Artificial Sequence

<400> SEQUENCE: 19

-continued

```
agtactgcga tcgcgttaac gct                                          23

<210> SEQ ID NO 20
<211> LENGTH: 44
<212> TYPE: DNA
<213> ORGANISM: Artificial Sequence
<220> FEATURE:
<221> NAME/KEY: misc_feature
<222> LOCATION: (1)..(44)
<223> OTHER INFORMATION: Fully synthetic DNA primer molecule

<400> SEQUENCE: 20

gcagtcgctg tgcgatacca cgtcggggcc cttctgctct tcca                   44

<210> SEQ ID NO 21
<211> LENGTH: 55
<212> TYPE: DNA
<213> ORGANISM: Artificial Sequence
<220> FEATURE:
<221> NAME/KEY: misc_feature
<222> LOCATION: (1)..(55)
<223> OTHER INFORMATION: Fully synthetic DNA primer molecule

<400> SEQUENCE: 21

agcgttaacg cgatcgcagt actttgaagc tccaaggatc ctgagcctca acaac       55

<210> SEQ ID NO 22
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Fully synthetic DNA primer molecule where
      u = uradine

<400> SEQUENCE: 22

gcagucgcug ugcgauacc                                               19

<210> SEQ ID NO 23
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Fully synthetic DNA primer molecule where
      u = uradine

<400> SEQUENCE: 23

agcgtuaacg cgaucgcagu acuu                                         24

<210> SEQ ID NO 24
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: Fully synthetic DNA primer molecule

<400> SEQUENCE: 24

gcggccgcct gcaggagcag attcaagtcg tccttcgatt tcatc                  45

<210> SEQ ID NO 25
<211> LENGTH: 45
<212> TYPE: DNA
<213> ORGANISM: Artificial Sequence
<220> FEATURE:
```

<221> NAME/KEY: misc_feature
<222> LOCATION: (1)..(45)
<223> OTHER INFORMATION: Fully synthetic DNA primer molecule

<400> SEQUENCE: 25
gcgagtaccg ctggcgatct aacgtcgggg cccttctgct cttcc 45

<210> SEQ ID NO 26
<211> LENGTH: 150
<212> TYPE: DNA
<213> ORGANISM: Artificial Sequence
<220> FEATURE:
<221> NAME/KEY: misc_feature
<222> LOCATION: (1)..(150)
<223> OTHER INFORMATION: Fully synthetic DNA primer molecule

<400> SEQUENCE: 26
aagtactgcg atcgcgttaa cgctttatca cgataccttc taccacatat cactaacaac 60
atcaacactc atcactctcg acgacatcca ctcgatcact actctcacac gaccgattaa 120
ctcctcatcc acgcggccgc ctgcaggagc 150

<210> SEQ ID NO 27
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Fully synthetic DNA primer molecule where
u = uradine

<400> SEQUENCE: 27
aaguactgcg aucgcguuaa cgcu 24

<210> SEQ ID NO 28
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Fully synthetic DNA primer molecule where
u = uradine

<400> SEQUENCE: 28
gcgaguaccg cuggcgauct a 21

<210> SEQ ID NO 29
<211> LENGTH: 11997
<212> TYPE: DNA
<213> ORGANISM: Artificial Sequence
<220> FEATURE:
<221> NAME/KEY: misc_feature
<222> LOCATION: (1)..(11997)
<223> OTHER INFORMATION: Synthetic plasmid DNA molecule

<400> SEQUENCE: 29
gtcccgcgtc aatattatta aaaaactcct acatttcttt ataatcaacc cgcactctta 60
taatctcttc tctactacta taataagaga gtttatgtac aaaataaggt gaaattatgt 120
ataagtgttc tggatattgg ttgttggctc catattcaca caacctaatc aatagaaaac 180
atatgtttta ttaaaacaaa atttatcata tatcatatat atatatatac atatatatat 240
atatatataa accgtagcaa tgcacgggca tataactagt gcaacttaat acatgtgtgt 300
attaagatga ataagagggt atccaaataa aaaacttgtt cgcttacgtc tggatcgaaa 360

-continued

```
ggggttggaa acgattaaat ctcttcctag tcaaaattga atagaaggag atttaatctc    420
tcccaatccc cttcgatcat ccaggtgcaa ccgtataagt cctaaagtgg tgaggaacac    480
gaaacaacca tgcattggca tgtaaagctc caagaatttg ttgtatcctt aacaactcac    540
agaacatcaa ccaaaattgc acgtcaaggg tattgggtaa gaaacaatca aacaaatcct    600
ctctgtgtgc aaagaaacac ggtgagtcat gccgagatca tactcatctg atatacatgc    660
ttacagctca caagacatta caaacaactc atattgcatt acaaagatcg tttcatgaaa    720
aataaaatag gccggacagg acaaaaatcc ttgacgtgta aagtaaattt acaacaaaaa    780
aaaagccata tgtcaagcta aatctaattc gttttacgta gatcaacaac ctgtagaagg    840
caacaaaact gagccacgca gaagtacaga atgattccag atgaaccatc gacgtgctac    900
gtaaagagag tgacgagtca tatacatttg gcaagaaacc atgaagctgc ctacagccgt    960
ctcggtggca taagaacaca agaaattgtg ttaattaatc aaagctataa ataacgctcg   1020
catgcctgtg cacttctcca tcaccaccac tgggtcttca gaccattagc tttatctact   1080
ccagagcgca gaagaacccg ggcccaccgt cttcggtacg cgctcactcc gccctctgcc   1140
tttgttactg ccacgtttct ctgaatgctc tcttgtgtgg tgattgctga gagtggttta   1200
gctggatcta gaattacact ctgaaatcgt gttctgcctg tgctgattac ttgccgtcct   1260
ttgtagcagc aaaatatagg gacatggtag tacgaaacga agatagaacc tacacagcaa   1320
tacgagaaat gtgtaatttg gtgcttagcg gtatttattt aagcacatgt tggtgttata   1380
gggcacttgg attcagaagt ttgctgttaa tttaggcaca ggcttcatac tacatgggtc   1440
aatagtatag ggattcatat tataggcgat actataataa tttgttcgtc tgcagagctt   1500
attatttgcc aaaattagat attcctattc tgtttttgtt tgtgtgctgt taaattgtta   1560
acgcctgaag gaataaatat aaatgacgaa attttgatgt ttatctctgc tcctttattg   1620
tgaccataag tcaagatcag atgcacttgt tttaaatatt gttgtctgaa gaaataagta   1680
ctgacagtat tttgatgcat tgatctgctt gtttgttgta acaaaattta aaaataaaga   1740
gtttcctttt tgttgctctc cttacctcct gatggtatct agtatctacc aactgacact   1800
atattgcttc tctttacata cgtatcttgc tcgatgcctt ctccctagtg ttgaccagtg   1860
ttactcacat agtctttgct catttcattg taatgcagat accaagcggg agctcgacgt   1920
ccctcagcag tcgctgtgcg ataccacgtc ggggcccttc tgctcttcca gcctgccgat   1980
gaacgccacc agcgggatgt tccggtccac cgggagcccg acctccgcct gcagcgcctc   2040
cttgttcagc gccttggcct ccacggccgt cgacacgtcg tacttcacgg cgatgtactt   2100
gtccctgctg gggtcccact cgctgacgtc catgccgttg acgatgccgg tgatgccggt   2160
gaggcgcatg atgttgtcga gctcgcagcc cctggcgatg ccggagatga gctcctcggc   2220
gtagtagggg ctgacggtga ggaccctgtc ggcctcgagg atcccggcct tcatccagtt   2280
gatcttccgg ccttccacgg gcttctcgta gccgtcgatg aaatcgaagg acgacttgaa   2340
tctctccggg aggttcagct ccgggtagtc ggagaaggcg aaccggccct ggtaggagat   2400
gttgtggatg cagaaagcgg tctttgcgtc cctgtagatg ccgtgggact ggtagttgct   2460
cttgaggtag cacgagagag ggccggtgtg ccagtcgttg cagacgaaca cgacgtcctc   2520
cccgtatggt ccggagaagt atgggttgtt gttgaggctc aggatccttg gagcttcaaa   2580
gtactgcgat cgcgttaacg ctttatcacg ataccttcta ccacatatca ctaacaacat   2640
caacactcat cactctcgac gacatccact cgatcactac tctcacacga ccgattaact   2700
cctcatccac gcggccgcct gcaggagcag attcaagtcg tccttcgatt tcatcgacgg   2760
```

-continued

```
ctacgagaag cccgtggaag gccggaagat caactggatg aaggccggga tcctcgaggc   2820
cgacagggtc ctcaccgtca gcccctacta cgccgaggag ctcatctccg gcatcgccag   2880
gggctgcgag ctcgacaaca tcatgcgcct caccggcatc accggcatcg tcaacggcat   2940
ggacgtcagc gagtgggacc ccagcaggga caagtacatc gccgtgaagt acgacgtgtc   3000
gacggccgtg gaggccaagg cgctgaacaa ggaggcgctg caggcggagg tcgggctccc   3060
ggtggaccgg aacatcccgc tggtggcgtt catcggcagg ctggaagagc agaagggccc   3120
cgacgttaga tcgccagcgg tactcgctga ggcctaggcg cggatccccc accctgcaat   3180
gtgaccctag acttgtccat cttctggatt ggccaactta attaatgtat gaaataaaag   3240
gatgcacaca tagtgacatg ctaatcacta taatgtgggc atcaaagttg tgtgttatgt   3300
gtaattacta attatctgaa taagagaaag agatcatcca tatttcttat cctaaatgaa   3360
tgtcacgtgt ctttataatt ctttgatgaa ccagatgcat ttattaacc aattccatat    3420
acatataaat attaatcata tataattaat atcaattggg ttagcaaaac aaatctagtc   3480
taggtgtgtt ttgctaatta ttgggggata gtgcaaaaag aaatctacgt tctcaataat   3540
tcagatagaa aacttaataa agtgagataa tttacataga ttgcttttat cctttgatat   3600
atgtgaaacc atgcatgata taaggaaaat agatagagaa ataatttttt acatcgttga   3660
atatgtaaac aatttaattc aagaagctag gaatataaat attgaggagt ttatgattat   3720
tattattatt ttgatgttca atgaagtttt ttttaatttc atatgaagta tacaaaaatt   3780
cttcatagat ttttgtttct atgccgtagt tatctttaat atatttgtgg ttgaagaaat   3840
ttattgctag aaacgaatgg attgtcaatt ttttttaaa gcaaatatat atgaaattat    3900
actgtatatt attttagtca tgattaaaat gtggccttaa ttgaatcatc tttctcattc   3960
attttttcaa aagcatatca ggatgattga tatttatcta ttttaaaaat taatttaagg   4020
gttcaaatta aatttaactt aaaagtgtcc taaccgtagt taaaggttta ctttaaaaaa   4080
atactatgaa aaatctaatc ttctatgaat cgaccggatt taaatccatc gttctggggc   4140
ctaacgggcc aagctttccg atcctacctg tcacttcatc aaaaggacag tagaaaagga   4200
aggtggcacc tacaaatgcc atcattgcga taaaggaaag gctatcattc aagatgcctc   4260
tgccgacagt ggtcccaaag atggaccccc acccacgagg agcatcgtgg aaaaagaaga   4320
cgttccaacc acgtcttcaa agcaagtgga ttgatgtgat acttccactg acgtaaggga   4380
tgacgcacaa tcccactatc cttcgcaaga cccttcctct atataaggaa gttcatttca   4440
tttggagagg acacgctgaa atcaccagtc tctctctaca agatcgggga tctctagcta   4500
gacgatcgtt tcgcatgatt gaacaagatg gattgcacgc aggttctccg gccgcttggg   4560
tggagaggct attcggctat gacattcggc tatgactggg cacaacagac aatcggctgc   4620
tctgatgccg ccgtgttccg gctgtcagcg caggggcgcc cggttctttt tgtcaagacc   4680
gacctgtccg gtgccctgaa tgaactgcag gacgaggcag cgcggctatc gtggctggcc   4740
acgacgggcg ttccttgcgc agctgtgctc gacgttgtca ctgaagcggg aagggactgg   4800
ctgctattgg gcgaagtgcc ggggcaggat ctcctgtcat ctcaccttgc tcctgccgag   4860
aaagtatcca tcatggctga tgcaatgcgg cggctgcata cgcttgatcc ggctacctgc   4920
ccattcgacc accaagcgaa acatcgcatc gagcgagcac gtactcggat ggaagccggt   4980
cttgtcgatc aggatgatct ggacgaagag catcaggggc tcgcgccagc cgaactgttc   5040
gccaggctca aggcgcgcat gcccgacggc gaggatctcg tcgtgaccca tggcgatgcc   5100
tgcttgccga atatcatggt ggaaaatggc cgcttttctg gattcatcga ctgtggccgg   5160
```

```
ctgggtgtgg cggaccgcta tcaggacata gcgttggcta cccgtgatat tgctgaagag   5220
cttggcggcg aatgggctga ccgcttcctc gtgctttacg gtatcgccgc tcccgattcg   5280
cagcgcatcg ccttctatcg ccttcttgac gagttcttct gagcgggact ctggggttcg   5340
aagaattccc gatcgttcaa acatttggca ataaagtttc ttaagattga atcctgttgc   5400
cggtcttgcg atgattatca tataatttct gttgaattac gttaagcatg taataattaa   5460
catgtaatgc atgacgttat ttatgagatg ggtttttatg attagagtcc cgcaattata   5520
catttaatac gcgatagaaa acaaaatata gcgcgcaaac taggataaat tatcgcgcgc   5580
ggtgtcatct atgttactag atcggggata tcgcgtgtct ttataattct ttgatgaacc   5640
agatgcattt tattaaccaa ttccatatac atataaatat taatcatata taattaatat   5700
caattgggtt agcaaaacaa atctagtcta ggtgtgtttt gctaattatt gggggatagt   5760
gcaaaaagaa atctacgttc tcaataattc agatagaaaa cttaataaag tgagataatt   5820
tacatagatt gcttttatcc tttgatatat gtgaaaccat gcatgatata aggaaaatag   5880
atagagaaat aattttttac atcgttgaat atgtaaacaa tttaattcaa gaagctagga   5940
atataaatat tgaggagttt atgattatta ttattatttt gatgttcaat gaagtttttt   6000
ttaatttcat atgaagtata caaaaattct tcatagattt ttgtttctat gccgtagtta   6060
tctttaatat atttgtggtt gaagaaattt attgctagaa acgaatggat tgtcaatttt   6120
tttttaaagc aaatatatat gaaattatac tgtatattat tttagtcatg attaaaatgt   6180
ggccttaatt gaatcatctt tctcattcat tttttcaaaa gcatatcagg atgattgata   6240
tttatctatt ttaaaaatta atttaagggt tcaaattaaa tttaacttaa aagtgtccta   6300
accgtagtta aaggtttact ttaaaaaaat actatgaaaa atctaatctt ctatgaatcg   6360
accgctgatc gatcgcggcc gctggcgcgc cttaattaag cggccgcatc gatcgtgaag   6420
tttctcatct aagcccccat ttggacgtga atgtagacac gtcgaaataa agatttccga   6480
attagaataa tttgtttatt gctttcgcct ataaatacga cggatcgtaa tttgtcgttt   6540
tatcaaaatg tactttcatt ttataataac gctgcggaca tctacatttt tgaattgaaa   6600
aaaaattggt aattactctt tctttttctc catattgacc atcatactca ttgctgatcc   6660
atgtagattt cccggacatg aagccattta caattgaata tatcctgccg ccgctgccgc   6720
tttgcacccg gtggagcttg catgttggtt tctacgcaga actgagccgg ttaggcagat   6780
aatttccatt gagaactgag ccatgtgcac cttcccccca acacggtgag cgacggggca   6840
acggagtgat ccacatggga cttttcctag cttggctgcc atttttgggg tgaggccgtt   6900
cgcggccgag ggcgcagcc cctgggggga tgggaggccc gcgttagcgg gccgggaggg   6960
ttcgagaagg gggggcaccc cccttcggcg tgcgcggtca cgcgcacagg gcgcagccct   7020
ggttaaaaac aaggtttata aatattggtt taaaagcagg ttaaaagaca ggttagcggt   7080
ggccgaaaaa cgggcggaaa cccttgcaaa tgctggattt tctgcctgtg gacagcccct   7140
caaatgtcaa taggtgcgcc cctcatctgt cagcactctg cccctcaagt gtcaaggatc   7200
gcgcccctca tctgtcagta gtcgcgcccc tcaagtgtca ataccgcagg gcacttatcc   7260
ccaggcttgt ccacatcatc tgtgggaaac tcgcgtaaaa tcaggcgttt tcgccgattt   7320
gcgaggctgg ccagctccac gtcgccggcc gaaatcgagc ctgcccctca tctgtcaacg   7380
ccgcgccggg tgagtcggcc cctcaagtgt caacgtccgc ccctcatctg tcagtgaggg   7440
ccaagttttc cgcgaggtat ccacaacgcc ggcggccggc cgcggtgtct cgcacacggc   7500
ttcgacggcg tttctggcgc gtttgcaggg ccatagacgg ccgccagccc agcggcgagg   7560
```

-continued

```
gcaaccagcc cggtgagcgt cggaaagggt cgatcgaccg atgcccttga gagccttcaa   7620
cccagtcagc tccttccggt gggcgcgggg catgactatc gtcgccgcac ttatgactgt   7680
cttctttatc atgcaactcg taggacaggt gccggcagcg ctctgggtca ttttcggcga   7740
ggaccgcttt cgctggagcg cgacgatgat cggcctgtcg cttgcggtat tcggaatctt   7800
gcacgccctc gctcaagcct tcgtcactgg tcccgccacc aaacgtttcg gcgagaagca   7860
ggccattatc gccggcatgg cggccgacgc gctgggctac gtcttgctgg cgttcgcgac   7920
gcgaggctgg atggccttcc ccattatgat tcttctcgct tccggcggca tcgggatgcc   7980
cgcgttgcag gccatgctgt ccaggcaggt agatgacgac catcagggac agcttcaagg   8040
atcgctcgcg gctcttacca gcctaacttc gatcattgga ccgctgatcg tcacggcgat   8100
ttatgccgcc tcggcgagca catggaacgg gttggcatgg attgtaggcg ccgccctata   8160
ccttgtctgc ctccccgcgt tgcgtcgcgg tgcatggagc cgggccacct cgacctgaat   8220
ggaagccggc ggcacctcgc taacggattc accactccaa gaattggagc caatcaattc   8280
ttgcggagaa ctgtgaatgc gcaaaccaac ccttggcaga acatatccat cgcgtccgcc   8340
atctccagca gccgcacgcg gcgcatctcg ggcagcgttg ggtcctggcc acgggtgcgc   8400
atgatcgtgc tcctgtcgtt gaggacccgg ctaggctggc ggggttgcct tactggttag   8460
cagaatgaat caccgatacg cgagcgaacg tgaagcgact gctgctgcaa aacgtctgcg   8520
acctgagcaa caacatgaat ggtcttcggt ttccgtgttt cgtaaagtct ggaaacgcgg   8580
aagtcagcgc cctgcaccat tatgttccgg atctgcatcg caggatgctg ctggctaccc   8640
tgtggaacac ctacatctgt attaacgaag cgctggcatt gaccctgagt gatttttctc   8700
tggtcccgcc gcatccatac cgccagttgt ttaccctcac aacgttccag taaccgggca   8760
tgttcatcat cagtaacccg tatcgtgagc atcctctctc gtttcatcgg tatcattacc   8820
cccatgaaca gaaatccccc ttacacggag gcatcagtga ccaaacagga aaaaaccgcc   8880
cttaacatgg cccgctttat cagaagccag acattaacgc ttctggagaa actcaacgag   8940
ctggacgcgg atgaacaggc agacatctgt gaatcgcttc acgaccacgc tgatgagctt   9000
taccgcagct gcctcgcgcg tttcggtgat gacggtgaaa acctctgaca catgcagctc   9060
ccggagacgg tcacagcttg tctgtaagcg gatgccggga gcagacaagc ccgtcagggc   9120
gcgtcagcgg gtgttggcgg gtgtcggggc gcagccatga cccagtcacg tagcgatagc   9180
ggagtgtata ctggcttaac tatgcggcat cagagcagat tgtactgaga gtgcaccata   9240
tgcggtgtga aataccgcac agatgcgtaa ggagaaaata ccgcatcagg cgctcttccg   9300
cttcctcgct cactgactcg ctgcgctcgg tcgttcggct gcggcgagcg gtatcagctc   9360
actcaaaggc ggtaatacgg ttatccacag aatcagggga taacgcagga aagaacatgt   9420
gagcaaaagg ccagcaaaag gccaggaacc gtaaaaaggc cgcgttgctg gcgtttttcc   9480
ataggctccg cccccctgac gagcatcaca aaaatcgacg ctcaagtcag aggtggcgaa   9540
acccgacagg actataaaga taccaggcgt ttccccctgg aagctccctc gtgcgctctc   9600
ctgttccgac cctgccgctt accggatacc tgtccgcctt tctcccttcg ggaagcgtgg   9660
cgctttctca tagctcacgc tgtaggtatc tcagttcggt gtaggtcgtt cgctccaagc   9720
tgggctgtgt gcacgaaccc cccgttcagc ccgaccgctg cgccttatcc ggtaactatc   9780
gtcttgagtc caacccggta agacacgact tatcgccact ggcagcagcc actggtaaca   9840
ggattagcag agcgaggtat gtaggcggtg ctacagagtt cttgaagtgg tggcctaact   9900
acggctacac tagaaggaca gtatttggta tctgcgctct gctgaagcca gttaccttcg   9960
```

```
gaaaaagagt tggtagctct tgatccggca aacaaaccac cgctggtagc ggtggttttt  10020

ttgtttgcaa gcagcagatt acgcgcagaa aaaaaggatc tcaagaagat cctttgatct  10080

tttctacggg gtctgacgct cagtggaacg aaaactcacg ttaagggatt ttggtcatga  10140

gattatcaaa aaggatcttc acctagatcc ttttaaatta aaaatgaagt tttaaatcaa  10200

tctaaagtat atatgagtaa acttggtctg acagttacca atgcttaatc agtgaggcac  10260

ctatctcagc gatctgtcta tttcgttcat ccatagttgc ctgactcccc gtcgtgtaga  10320

taactacgat acgggagggc ttaccatctg gccccagtgc tgcaatgata ccgcgagacc  10380

cacgctcacc ggctccagat ttatcagcaa taaaccagcc agccggaagg gccgagcgca  10440

gaagtggtcc tgcaacttta tccgcctcca tccagtctat taattgttgc cgggaagcta  10500

gagtaagtag ttcgccagtt aatagtttgc gcaacgttgt tgccattgct gcaggtcggg  10560

agcacaggat gacgcctaac aattcattca agccgacacc gcttcgcggc gcggcttaat  10620

tcaggagtta aacatcatga gggaagcggt gatcgccgaa gtatcgactc aactatcaga  10680

ggtagttggc gtcatcgagc gccatctcga accgacgttg ctggccgtac atttgtacgg  10740

ctccgcagtg gatggcggcc tgaagccaca cagtgatatt gatttgctgg ttacggtgac  10800

cgtaaggctt gatgaaacaa cgcggcgagc tttgatcaac gaccttttgg aaacttcggc  10860

ttcccctgga gagagcgaga ttctccgcgc tgtagaagtc accattgttg tgcacgacga  10920

catcattccg tggcgttatc cagctaagcg cgaactgcaa tttggagaat ggcagcgcaa  10980

tgacattctt gcaggtatct tcgagccagc cacgatcgac attgatctgg ctatcttgct  11040

gacaaaagca agagaacata gcgttgcctt ggtaggtcca gcggcggagg aactctttga  11100

tccggttcct gaacaggatc tatttgaggc gctaaatgaa accttaacgc tatggaactc  11160

gccgcccgac tgggctggcg atgagcgaaa tgtagtgctt acgttgtccc gcatttggta  11220

cagcgcagta accggcaaaa tcgcgccgaa ggatgtcgct gccgactggg caatggagcg  11280

cctgccggcc cagtatcagc ccgtcatact tgaagctagg caggcttatc ttggacaaga  11340

agatcgcttg gcctcgcgcg cagatcagtt ggaagaattt gttcactacg tgaaaggcga  11400

gatcaccaag gtagtcggca aataatgtct aacaattcgt tcaagccgac gccgcttcgc  11460

ggcgcggctt aactcaagcg ttagatgctg caggcatcgt ggtgtcacgc tcgtcgtttg  11520

gtatggcttc attcagctcc ggttcccaac gatcaaggcg agttacatga tcccccatgt  11580

tgtgcaaaaa agcggttagc tccttcggtc ctccgatcga ggatttttcg gcgctgcgct  11640

acgtccgcga ccgcgttgag ggatcaagcc acagcagccc actcgacctt ctagccgacc  11700

cagacgagcc aagggatctt tttggaatgc tgctccgtcg tcaggctttc cgacgtttgg  11760

gtggttgaac agaagtcatt atcgcacgga atgccaagca ctcccgaggg gaaccctgtg  11820

gttggcatgc acatacaaat ggacgaacgg ataaaccttt tcacgccctt ttaaatatcc  11880

gattattcta ataaacgctc ttttctctta ggtttacccg ccaatatatc ctgtcaaaca  11940

ctgatagttt aaactgaagg cgggaaacga caatctggcg cgccgctagc ctgcagg     11997
```

<210> SEQ ID NO 30
<211> LENGTH: 10
<212> TYPE: DNA
<213> ORGANISM: Artificial sequence
<220> FEATURE:
<221> NAME/KEY: misc_feature
<222> LOCATION: (1)..(10)
<223> OTHER INFORMATION: Terminal, single-stranded DNA segment

<400> SEQUENCE: 30
gatctcttgg 10

<210> SEQ ID NO 31
<211> LENGTH: 10
<212> TYPE: DNA
<213> ORGANISM: Artificial sequence
<220> FEATURE:
<221> NAME/KEY: misc_feature
<222> LOCATION: (1)..(10)
<223> OTHER INFORMATION: Terminal, single-stranded DNA segment

<400> SEQUENCE: 31
ctagagaacc 10

<210> SEQ ID NO 32
<211> LENGTH: 10
<212> TYPE: DNA
<213> ORGANISM: Artificial sequence
<220> FEATURE:
<221> NAME/KEY: misc_feature
<222> LOCATION: (1)..(10)
<223> OTHER INFORMATION: Terminal, single-stranded DNA segment

<400> SEQUENCE: 32
gtgcaatagc 10

<210> SEQ ID NO 33
<211> LENGTH: 10
<212> TYPE: DNA
<213> ORGANISM: Artificial sequence
<220> FEATURE:
<221> NAME/KEY: misc_feature
<222> LOCATION: (1)..(10)
<223> OTHER INFORMATION: Terminal, single-stranded DNA segment

<400> SEQUENCE: 33
ccaagagatc 10

<210> SEQ ID NO 34
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Bridging single-stranded DNA oligomer

<400> SEQUENCE: 34
gctattgcac gatctcttgg 20

<210> SEQ ID NO 35
<211> LENGTH: 1745
<212> TYPE: DNA
<213> ORGANISM: Artificial sequence
<220> FEATURE:
<221> NAME/KEY: misc_feature
<222> LOCATION: (1)..(1745)
<223> OTHER INFORMATION: LIC inserted DNA molecule

<400> SEQUENCE: 35
gcagtcgctg tcgttaccat ggcaatggag gttggggaga tgtctcagcc ggaggcgacg 60
gcgagtcttc tctctctcgc ttccgccact cagcaaccgt acgtctccga gctcctctct 120
ttcactcttg atcgtctcca caaggaaccg gagctgcttc gagtggatgc ggagcggatt 180
cagaggcaaa tgcaagaggt ggctgttgga aattaccgcg cgtttatcac cgctgctgat 240
gctttgcttg cgatccgtca ggaagtttct tccattgata agcatctcga gtctctgatt 300

-continued

```
ggcgaagtcc caaaactaac gtctggttgc actgaattta tcgattctgc tgagaatatt    360
ttggagaaga ggaagatgaa ccaagcattg ctggcaaatc acagcactct tcttgacttg    420
cttgagattc ctcagcttat ggacacatgc gtgaggaatg gaaattttga tgaggctctt    480
gacctggaag catttgtatc gaaacttgct accctgcatc ccaaattgcc agttatccaa    540
gcacttgcag cggaggttag acaaacaact cagtcacttc tctcacagct tctccagaaa    600
ctacgctcaa atatacagtt accagaatgt ctccgcatta ttggatactt acgccgaata    660
ggtgtctttg gcgagtatga aatgcgatta cagttcttaa gatgccgaga ggcatggctc    720
actggaattc ttgaggattt agatcagaaa aatgcctatg agtatttaaa aggcatgata    780
aactgtcaca gaatgcacct atttgacgtg gttaaccaat atcgagctat attttctgat    840
gatacatctg ggagcgaaga aaattatgat ggtggacttt tgtttagctg ggccatgcat    900
caaataacat cacacctgaa gactctaaaa atcatgcttc caaagattac tgaaggagga    960
tctctatcaa atattttgga tcagtgcatg tactgtgcga tggggcttgg tggggttggg   1020
ctagacttcc ggggtctgct tcctccactt tttgaagagg cggttctaaa cttattctcc   1080
aagaacatga gtacagcagt tgagaatttt cagttagttt tggattcaca tcgatgggtt   1140
ccattaccat ctgttggctt tccttcaagt ggtattaatg aagatagcaa ggatgacgtc   1200
acacctccat catacttgat ggagcacccg ccacttgcag ttttcataaa tggggtatct   1260
tctgctttga acgaattacg tccttgtgcc ccgctaagtc taaagaatgt tgttgctcat   1320
gaactgatca aaggactcca ggccgtgtct gactccttac taagatacaa tacaactcgg   1380
atgcttcgac tcagtgaatc caatctattc ctttcacttt gccgagcttt tgtcgaggtg   1440
gtttttccac attgcgccac atgctttggc cgatgttatc caggtggtgc cacaatcgtt   1500
atggatgcca agagtgcata cgaaggtctg ggtcgcatct tagctgcatc gtcctctcaa   1560
gaaccatcca acaaatctcc aaaggtcatc agcacggaca caaaggatgc atcagagaat   1620
ggtgtagcct cccaacctga agaaaaacaa gccgagaatc caaacgcgaa agaagaagat   1680
aacagtccca ttcctttgca gactcctgag ataacacccg agtcttagaa cccagcggta   1740
ctcgc                                                               1745
```

METHODS FOR LIGATION INDEPENDENT CLONING OF DNA

CROSS REFERENCE TO RELATED APPLICATIONS

This application claims benefit of priority under 35 U.S.C. 119(e) to provisional application Ser. No. 60/634,779 filed Dec. 9, 2004.

INCORPORATION OF SEQUENCE LISTING

Two copies of the sequence listing (Seq. Listing Copy 1 and Seq. Listing Copy 2) and a computer-readable form of the sequence listing, all on CD-R's, each containing the file named 38-21(53344)B_seqListing.txt, which is 71,680 bytes (measured in MS-WINDOWS) and was created on Mar. 26, 2008, are hereby incorporated by reference.

BACKGROUND OF THE INVENTION

Disclosed herein are methods for assembling DNA molecules in a predetermined order in a DNA construct and methods of using such constructs.

Many methods have been developed and used for assembling DNA molecules. Examples of these are cloning by restriction endonuclease digestion followed by ligation of compatible ends, T-A cloning directly from a polymerase chain reaction product, recombination-based cloning and ligation-independent cloning of polymerase chain reaction products.

Ligation-independent cloning is a highly efficient and cost effective method for assembling DNA molecules using non-covalent, bi-molecular association of terminal, single-stranded DNA segments to assemble DNA molecules. Terminal, single-stranded DNA segments can be incorporated into DNA molecules by a variety of methods. Examples of methods for producing terminal, single-stranded DNA segments include, but are not limited to, (a) ligation of adapter molecules containing a terminal, single-stranded DNA segment, (b) incorporation of nicking endonuclease sites during polymerase chain reaction, (c) exonuclease digestion and (d) incorporation of deoxy-uridine residues during polymerase chain reaction which can be deaminated by the enzyme, uracil-N glycosylase. Such methods are described in Aslanidis and de Jong, Nucleic Acids Research, 18 (20), pages 6069-6074 (1990); U.S. Pat. No. 5,580,759 (Yang, et al.); U.S. Pat. No. 5,137,814 (Rashtchian et al.) and U.S. Pat. No. 6,495,318 (Harney), all of which are incorporated herein by reference. Once assembled, the DNA construct is repaired and replicated in the bacterial host using the host's endogenous systems.

Conventional cloning methods can be time consuming and often rely on a series of sub cloning steps to produce the final DNA construct. DNA constructs used in plant transformation contain a number of necessary components for replication, transformation and selection. For example, the DNA construct must have an origin of replication and selectable marker for the bacterial hosts, both for *Escherichia coli* as well as *Agrobacterium tumefaciens*. For plant transformation, the construct must also contain a right and left border sequence to allow for the transfer and stable incorporation of the DNA from *Agrobacterium* to the plant host cells. The DNA construct will also usually contain a eukaryotic promoter, which drives the expression of protein coding sequences and transcriptional terminators. DNA constructs typically also comprise selectable or screenable markers used in identifying the transformed plant host cells. The final DNA construct can be quite large. Therefore, a need exists for developing simpler and widely applicable methods for producing constructs used in plant transformation.

SUMMARY OF THE INVENTION

This invention provides methods for assembling DNA molecules in a predetermined order to produce a DNA construct useful in *Agrobacterium* mediated transformation in plants. More particularly, the method employs ligation independent cloning of separate DNA elements where one of the DNA elements contains T-DNA borders from *Agrobacterium tumefaciens*. One aspect of this invention provides a method for assembling DNA molecules in a predetermined order in a DNA construct, said method comprising:

(a) providing at least two double-stranded DNA molecules each of which has terminal, single-stranded, DNA segments in a length of from 10 to 30 nucleotides extending from the 5' and 3' termini, wherein terminal, single-stranded DNA segments on each double-stranded DNA molecule do not hybridize to each other, wherein a terminal, single-stranded DNA segment on a first and second double-stranded DNA molecule hybridize to each other or to a single-stranded DNA oligomer of from about 20 to at least about 40 nucleotides to allow for specific annealing and linkage of the DNA molecules in a predetermined order, and wherein one of said double-stranded DNA molecules contains T-DNA borders from *Agrobacterium tumefaciens*; and (b) incubating said DNA molecules under conditions suitable to promote the specific annealing and assembling of the DNA molecules in a predetermined order.

In an embodiment of the method, one of the molecules is a plasmid backbone which contains right and left T-DNA borders. Sense and antisense versions of a construct can be generated by repeating steps (a) and (b) with one of the DNA molecules modified with terminal, single-stranded DNA segments interchanged to the opposite sides of the double-stranded DNA molecule. A DNA construct containing an inverted repeat can be produced using DNA molecules that comprise the same or a portion of the same DNA molecule with two sets of terminal, single-stranded DNA segments interchanged to the opposite sides of the double-stranded DNA molecule. The resulting DNA molecules are then capable of being assembled in a manner that produces the inverted repeat. Furthermore, the terminal, single-stranded DNA segments for the inverted repeat construct can be designed in such a manner as to allow the production of restriction endonuclease sites within the region joining the repeats. This enhancement allows one skilled in the art to digest and cleave the DNA construct in between the repeats facilitating the sequence confirmation of the repeat region. Without cleavage of the construct in this manner, DNA sequencing becomes contaminated by conflicting information as the sequence reaction proceeds through the repeat region.

The DNA molecules in this method encodes a biological functionality selected from the group consisting of promoter or portion thereof, origin of replication, selectable marker, transcriptional regulatory element, cellular localization signal, protein processing sequence, plastid targeting sequence, structural gene or molecule thereof, transcription termination signal, translational regulatory signal, recombination elements, mutagenized genes, artificial genes, chimeric genes, protein domain encoded regions or portion there of, tagging epitopes, DNA spacer regions, synthetic multiple cloning sites, unique restriction enzyme or DNA cleavage sites, and sites for covalent or noncovalent attachment of a biological or a chemical molecule.

Another aspect of this invention provides a method for assembling an inverted repeat of DNA molecules in a predetermined order in a DNA construct, said method comprising: (a) providing at least two double-stranded DNA molecules each of which has terminal, single-stranded, DNA segments in a length of from 10 to 30 nucleotides extending from the 5' and 3' termini, wherein terminal, where single-stranded DNA segments on each double-stranded DNA molecule do not hybridize to each other, and where a terminal, single-stranded DNA segments on a first and a second double-stranded DNA molecule hybridize to each other or to a single-stranded DNA oligomer of from about 20 to at least about 40 nucleotides to allow for specific annealing and linkage of the DNA molecules in a predetermined order, and where two of the at least two double-stranded DNA molecules are substantially identical and have a common terminal single-stranded DNA segment that allows assembly of an inverted repeat of DNA; and (b) incubating said DNA molecules under conditions suitable to promote the specific annealing and assembling of the DNA molecules in an inverted repeat order.

The terminal, single-stranded DNA segments for the inverted repeat construct can be designed in such a manner as to allow the production of restriction endonuclease sites within the region joining the repeats. This enhancement allows one skilled in the art to digest and cleave the DNA construct in between the repeats facilitating the sequencing of the repeat region.

BRIEF DESCRIPTION OF THE DRAWINGS

FIGS. 1*a* and 1*b* illustrates alternative methods to assemble DNA molecules using terminal, single-stranded DNA segments. Terminal single stranded segments labeled 2, 3, 8 and 9 are represented by SEQ ID NOS: 30, 31, 32 and 33, respectively. A single-stranded oligomer used to bridge single-stranded DNA segments 8 and 10 is represented as SEQ ID NO: 34.

DETAILED DESCRIPTION OF THE INVENTION

Figure 2:
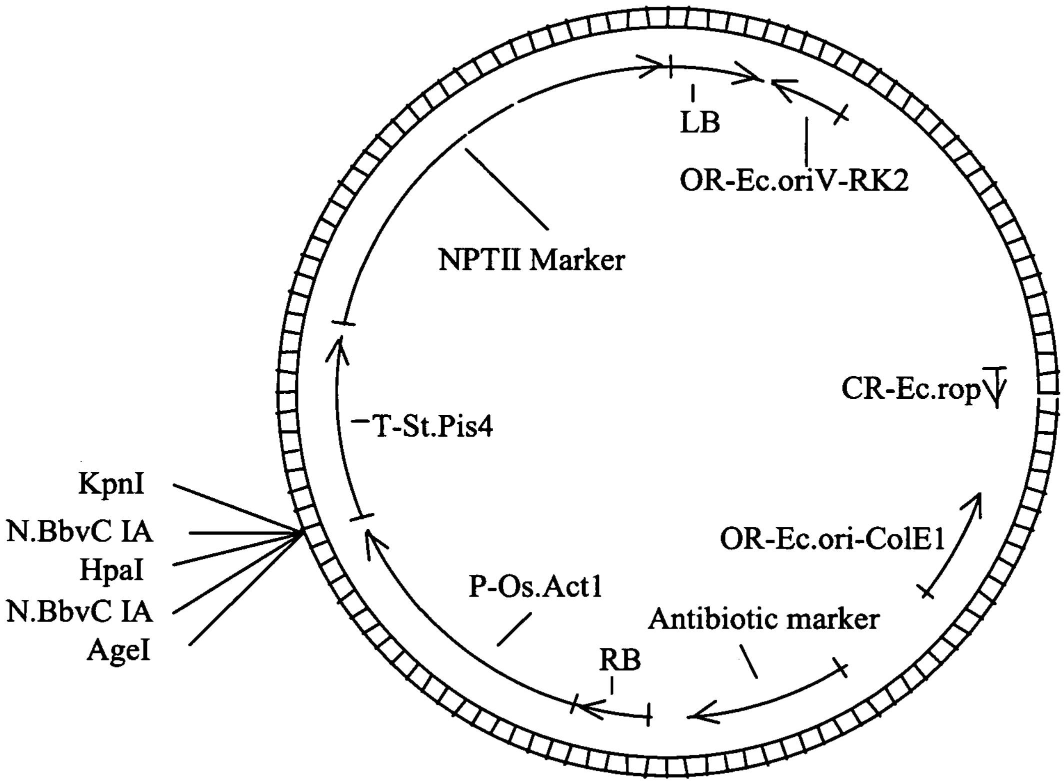
FIG. 2 illustrates a plasmid backbone useful in the methods of this invention. The circularized plasmid backbone is provided as SEQ ID NO: 1.
Figure 6:
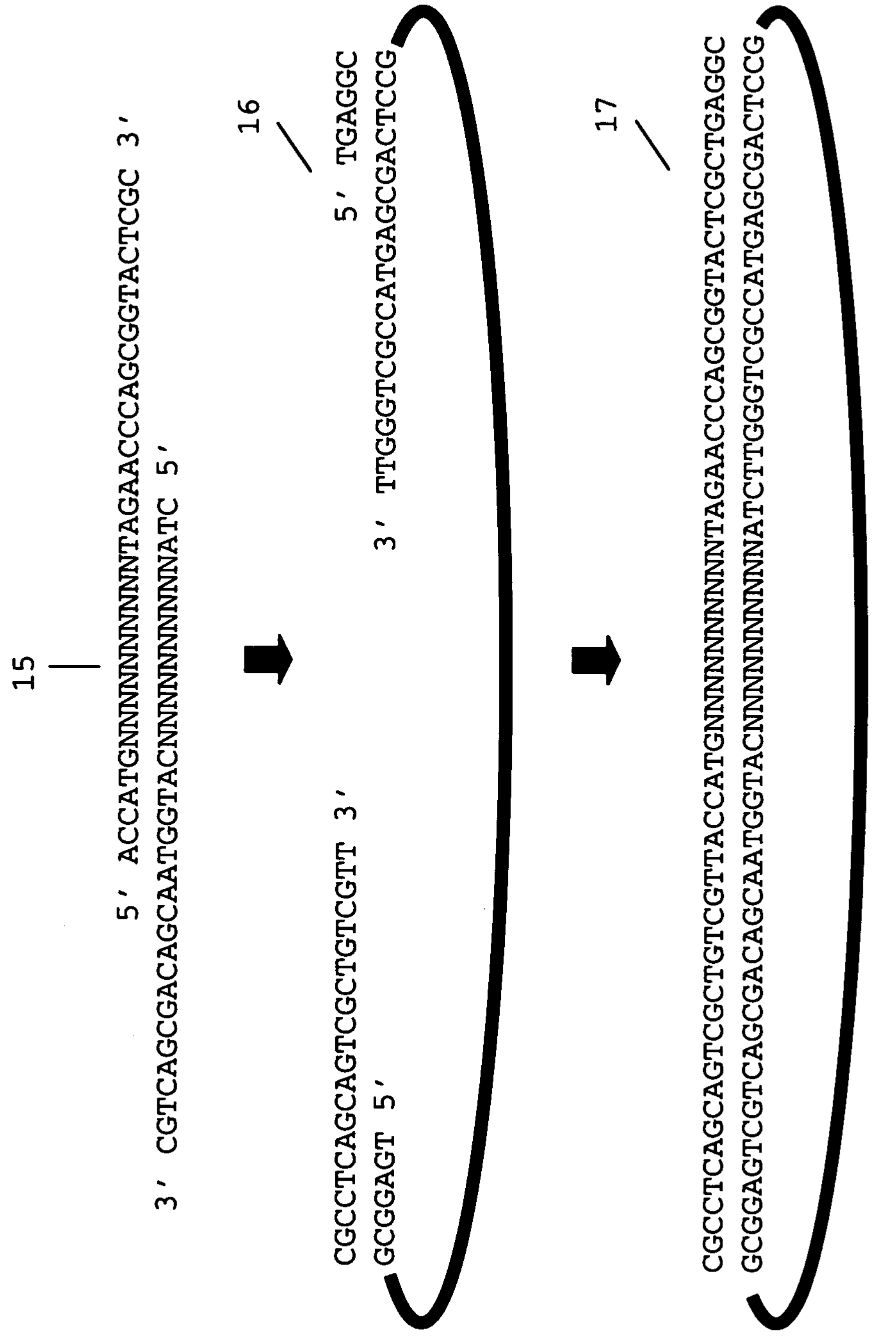
FIG. 6 illustrates the assembly of DNA molecules into a plasmid.
Figure 8:
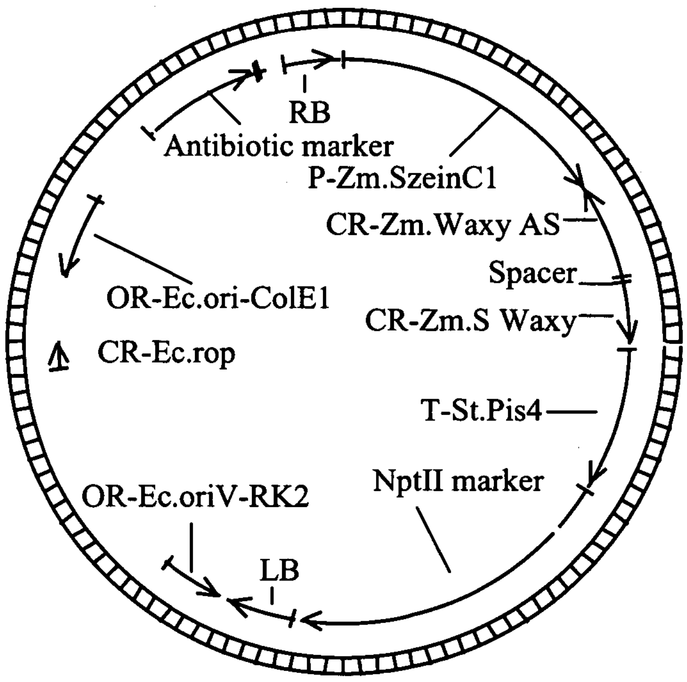
FIG. 8 illustrates a DNA construct assembled from three DNA molecules and is presented as SEQ ID NO; 18.
Figure 9:
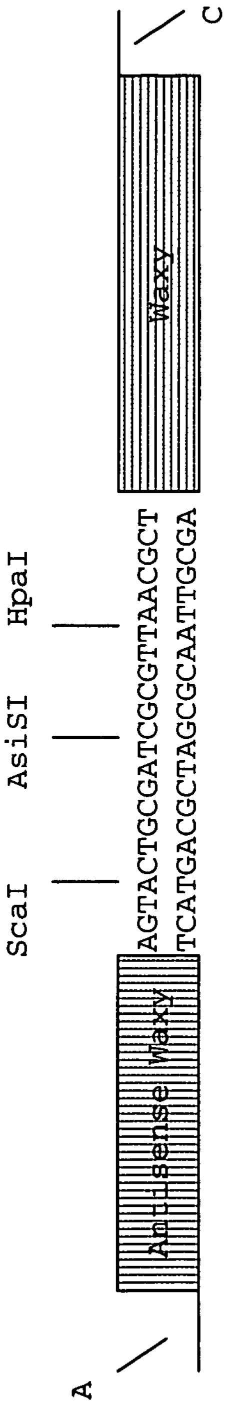
FIG. 9 illustrates the spacer region within an inverted repeat. The region between the repeats (referred herein as TAG-ART.Spacer Region 2) is provided as SEQ ID NO: 19.
Figure 11:
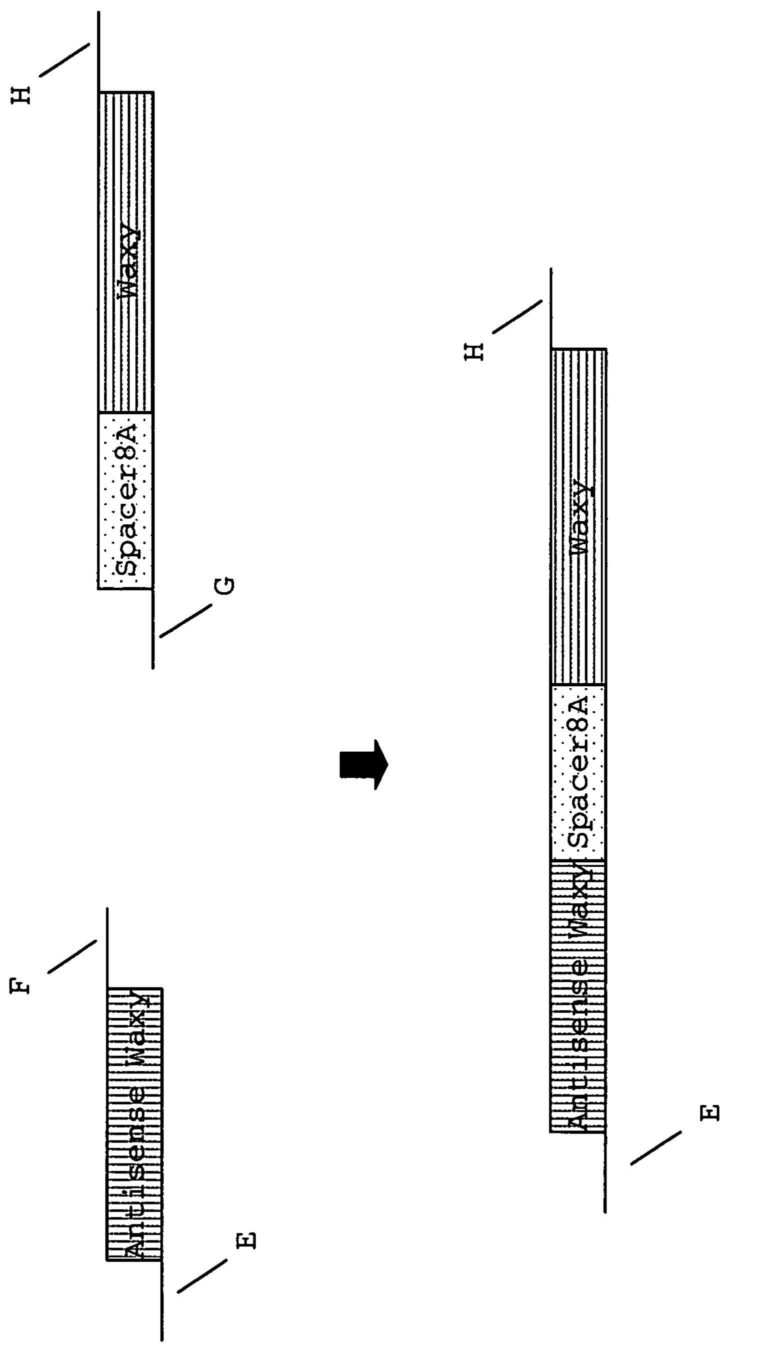
FIG. 11 illustrates an assembly scheme for producing an inverted repeat. The terminal, single-stranded DNA segments, E, F, G and H are produced using the primers presented as SEQ ID NOS: 21 and 23 (for terminal, single-stranded DNA segment E); SEQ ID NOS: 20 and 22 (for terminal, single-stranded DNA segment F); SEQ ID NO: 27 (for terminal, single-stranded DNA segment G) and; SEQ ID NOS: 25 and 28 (for terminal, single-stranded DNA segment H).

The sequence listing comprises:

SEQ ID NO: 1—nucleotides in the plasmid backbone shown in FIG. 2;

SEQ ID NO: 2—nucleotides in an adapter molecule;

SEQ ID NO: 3—nucleotides coding for *A. thaliana* CGPG3721;

SEQ ID NO: 4-7—of nucleotides for primers;

SEQ ID NO: 8—nucleotides in the assembled plasmid shown in FIG. 6;

SEQ ID NO: 9—nucleotides coding for a segment of maize Waxy;

SEQ ID NO: 10-17—nucleotides for primers;

SEQ ID NO: 18—nucleotides in the assembled plasmid shown in FIG. 8;

SEQ ID NO: 19—nucleotides in a spacer region between inverted repeats as illustrated in FIG. 9;

SEQ ID NO: 20-25—nucleotides for primers;

SEQ ID NO: 26—nucleotides in a spacer region between inverted repeats as illustrated in FIG. 11;

SEQ ID NO: 27-28—nucleotides for primers; and

Figure 12:
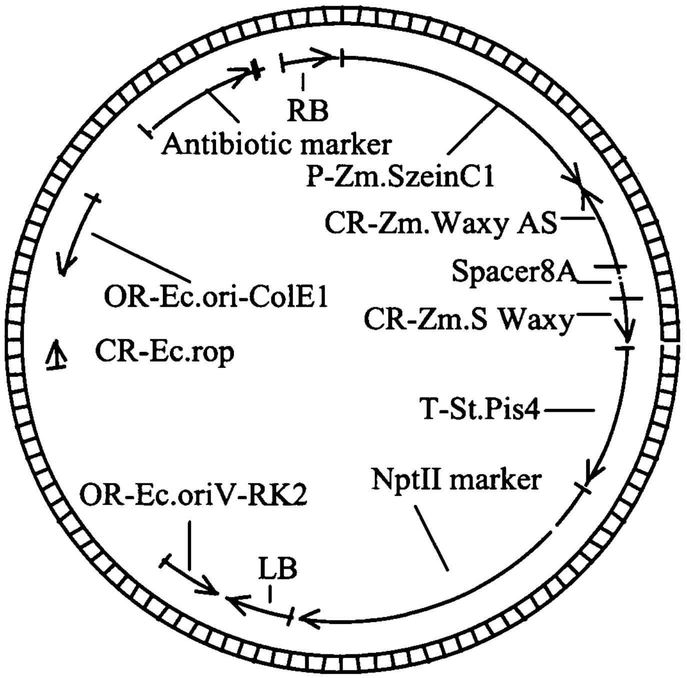
FIG. 12 illustrates a DNA construct assembled from three DNA molecules and is presented as SEQ ID NO: 29.

SEQ ID NO: 29—nucleotides in the assembled plasmid shown in FIG. 12.

SEQ ID NO: 30—nucleotide sequence of terminal, single-stranded DNA segment, indicated by "2" in FIG. 1*a*.

SEQ ID NO: 31—nucleotide sequence of terminal, single-stranded DNA segment, indicated by "3" in FIG. 1*a*.

SEQ ID NO: 32—nucleotide sequence of terminal, single-stranded DNA segment, indicated by "8" in FIG. 1*b*.

SEQ ID NO: 33—nucleotide sequence of terminal, single-stranded DNA segment, indicated by "9" in FIG. 1*b*.

SEQ ID NO: 34—nucleotide sequence of a single-stranded oligomer 6 used to bridge terminal, single-stranded DNA segment 8 and 9 in FIG. 1*b*.

SEQ ID NO: 35—nucleotide sequence of an inserted DNA molecule, indicated as "15" in FIG. 6 represented by nucleotide 10,258 through nucleotide 1 of the plasmid presented as SEQ ID NO: 8.

As used herein "T-DNA" means transfer-DNA which integrates into a genome by *Agrobacterium*-mediated transformation. For *Agrobacterium*-mediated transformation T-DNA is typically flanked by T-DNA borders within a plasmid, for example, a binary vector plasmid which is transferred into an *Agrobacterium tumefaciens* strain carrying a disarmed tumor inducing (Ti) plasmid.

As used herein, the term "assembling" means a process in which DNA molecules are joined through hybridization of terminal, single-stranded DNA segments. The terminal, single-stranded DNA segments are preferably non-palindromic sequences, which can be produced either through polymerase chain reaction or ligation. The terminal, single-stranded DNA segments enable users to specify the precise organization and orientation of DNA molecules in a construct. In one embodiment of the method, the terminal, single-stranded DNA segments are added during polymerase chain reaction. Oligonucleotides are synthesized to contain a sequence of nucleotides, which will be complementary to another terminal, single-stranded DNA segment. Within the oligonucleotide sequence, uridine residues are substituted for thiamine residues in specific positions. Amplification is performed using a thermal stable polymerase capable of reading through uridine residues in the template. After polymerase chain reaction, the resulting product is treated with Uracil-DNA glycosylase (UDG), which specifically deaminates the uridine residues. The DNA strand containing the uridine residues becomes unstable after UDG treatment in the positions containing uridine. Following heat treatment, the double-stranded DNA molecule becomes single-stranded in the region containing the uridine residues. In another embodiment of the method, a terminal single-stranded DNA segment can be introduced using nicking endonucleases. Nicking endonucleases hydrolyze only one strand of the double-stranded DNA molecule. A nicking endonuclease site can be incorporated into the DNA molecule either through conventional cloning methods available to those skilled in the art or through polymerase chain reaction. Oligonucleotides for polymerase chain reaction can be designed to contain the recognition sequence for any of several commercially available nicking endonucleases. After polymerase chain reaction amplification, the polymerase chain reaction product is treated with the appropriate nicking enzyme. After enzyme treatment, the product is incubated at a temperature sufficient to cause loss of the hydrolyzed strand, resulting in a terminal, single-stranded DNA segment. In another embodiment of the method, terminal, single-stranded DNA segments can be introduced by ligation of adapter molecules to the DNA molecule. Assembling of the DNA molecules can occur directly through the hybridization of the terminal, single-stranded DNA segments.

For example, as depicted in FIG. 1*a*, DNA molecule 1 with a terminal, single-stranded DNA segment 2 (presented as SEQ ID NO: 30) anneals to the terminal, single-stranded DNA segment 3 (presented as SEQ ID NO: 31) of DNA molecule 4. Alternatively, an oligomer can be used to bridge two terminal, single-stranded DNA segments, as depicted in FIG. 1*b* where single-stranded oligomer 6 (presented as SEQ ID NO: 34) is used to bridge DNA molecules 7 and 10 by annealing to their respective terminal, single-stranded DNA segments 8 (presented as SEQ ID NO: 32) and 9 (presented as SEQ ID NO: 33).

As used herein, the term "DNA construct" refers to an assembled DNA molecule, for example, an assembled plasmid which is capable of autonomous replication within the bacterial hosts, *Escherichia coli* and *Agrobacterium tumefaciens* and contains elements necessary for stable integration of DNA contained within the plasmid into the plant host cells.

As used herein, the term "plasmid backbone" describes a DNA molecule, which contains at least the elements necessary for autonomous replication within the bacterial hosts, *Escherichia coli* and *Agrobacterium tumefaciens* and contains right and left borders necessary for stable integration of DNA into the plant host cell. The plasmid backbone will also contain a selectable marker for bacterial selection and a different selectable marker used in identifying transformed plant cells. FIG. 2 and Table 1 illustrate DNA elements that are typically contained in a plasmid backbone. For replication in the bacterial host cells, two origins of replication are present. One origin of replication is used for plasmid replication in an *Escherichia coli* host cell (OR-Ec.ori-ColE1) A repressor of the ColE1 origin of replication (rop) is also present to keep the copy number of the plasmid low to minimize any potential toxic effects from the assembled DNA construct. Another origin of replication is provided for replication within the *Agrobacterium* host cell, the RK2 vegetative origin of replication. (OR-Ec.oriV-RK2) A gene conferring resistance to the antibiotic, spectinomycin and its associated promoter and terminator is used for selection of bacterial transformants and to maintain the plasmid within the bacterial hosts (antibiotic marker). Right and left borders (RB) and (LB), essential for the transfer and integration of DNA from the *Agrobacterium* host to the plant cell are contained within the backbone.

During *Agrobacterium*-mediated transformation DNA between the right and left borders will be transferred and integrated into the DNA of the host plant cell. Between the right and left borders in FIG. 2, there is an nptII (neomycin phosphotransferase II) selectable marker transcription unit and an incomplete transcription unit. The nptII selectable marker transcription unit confers resistance to the antibiotic kanamycin and is used for selecting transformed plant host cells. The nptII unit comprises the cauliflower mosaic virus 35S RNA gene promoter, the nptII coding region and nopaline synthase transcriptional terminator. The incomplete transcription unit comprises a rice actin promoter unit which includes a 5'UTR exon and intron (P-Os.Act). The promoter is used to control the transcription of an operably linked DNA molecule (for example, a peptide coding region, an antisense DNA molecule or an inverted repeat DNA molecule) that can be inserted between the promoter and the transcriptional terminator of the potato proteinase inhibitor II gene (T-St.Pis4). The elements of the plasmid are summarized in Table 1 where the element position identifies a position in SEQ ID NO: 1.

TABLE 1

| Element Name | Position | Element Function |
|---|---|---|
| RB | 5235-5591 | Right border sequence for T-DNA transfer |
| P-Os.Act | 5609-7009 | Promoter from the rice actin gene, act1 including first exon and first intron and flanking UTR exon from the rice actin gene, act1. |
| T-St.Pis4 | 7084-8026 | Transcription termination sequence of the potato proteinase inhibitor II gene. |
| NptII marker | 8075-9507 | transcription unit for nptII marker including promoter and 5'UTR for the CaMV 35S RNA, coding region for nptII from |

TABLE 1-continued

| Element Name | Position | Element Function |
|---|---|---|
| | | *E. coli* and transcription termination sequence of from nopaline synthase gene from *Agrobacterium*. |
| IG-St.Pis4 | 9519-10265 | Intergenic region of the potato proteinase inhibitor II gene. |
| LB | 39-480 | Left border sequence for T-DNA transfer. |
| OR-Ec.oriV-RK2 | 567-963 | Vegetative origin of replication used by *Agrobacterium tumefaciens*. |
| CR-Ec.rop | 2472-2663 | Coding region for the repressor of the primer for the ColE1 origin of replication. |
| OR-Ec.ori-ColE1 | 3091-3679 | Minimal origin of replication from the *Escherichia coli* plasmid, ColE1. |
| Antibiotic marker | 4210-5098 | Transcription unit for antibiotic marker including promoter for Tn7 adenyltransferase, coding region for Ec.aadA-SPC/STR, transcription terminator region from Tn7 adenyltransferase conferring spectinomycin and streptomycin resistance. |

As used herein, the term “substantially identical” describes two DNA molecules which contain DNA sequence that has been derived from the same DNA molecule and contain a region of identity that is at least 19 nucleotides in length.

In the methods of this invention, any DNA molecule can be inserted into a plasmid, i.e., a plasmid backbone. Different promoters, transcriptional terminators and introns can be assembled with a plurality of coding and non-coding DNAs to address a number of user-defined criteria (for example, the expression of a protein encoding DNA or the expression of an inverted repeat). Multiple transcription units (often called gene cassettes) can also be assembled into the plasmid backbone. The methods of this invention can be used to assemble DNA constructs in a high throughput production manner. Any DNA molecule can be designed to contain unique terminal, single-stranded DNA segments, allowing assembly with other DNA molecules in a specific order and orientation. A single plasmid backbone can be used as a template to assemble many different DNA constructs in a production facility by incorporating compatible terminal, single-stranded DNA segments in a collection of DNA molecules chosen for assembly.

The DNA molecules for insertion into a plasmid backbone can be any DNA molecule derived from any source or produced by any means including, but not limited to, amplification such as by polymerase chain reaction or through the use of other polymerases, isolation from natural sources, chemical synthesis, shearing or restriction digest of larger DNA molecules (such as genomic or cDNA), transcription, reverse transcription, and the like. Such DNA molecules may be derived from or comprise DNA from any natural sources such as cells (for example, prokaryotic cells or eukaryotic cells), viruses, tissues, organs (such as organs from any animal, plant, or other source), and organisms or may be derived from or comprise DNA from non-natural or synthetic sources (for example, derivative DNA molecules).

Alternative terminal, single-stranded DNA segments can be created by annealing DNA oligos or DNA adapters that contain a region of homology to a terminal, single-stranded DNA segment. The single DNA strand of the duplex DNA molecule containing the terminal, single-stranded DNA segment can be altered by annealing an oligo to the existing terminal, single-stranded DNA segment.

The following examples are provided to assist those skilled in the art to practice methods of this invention. The examples should not be construed to unduly limit the invention because modifications and variations of the embodiments discussed herein will be apparent to those of ordinary skill in the art without departing from the spirit or scope of the disclosed invention.

Example 1

Figure 3:
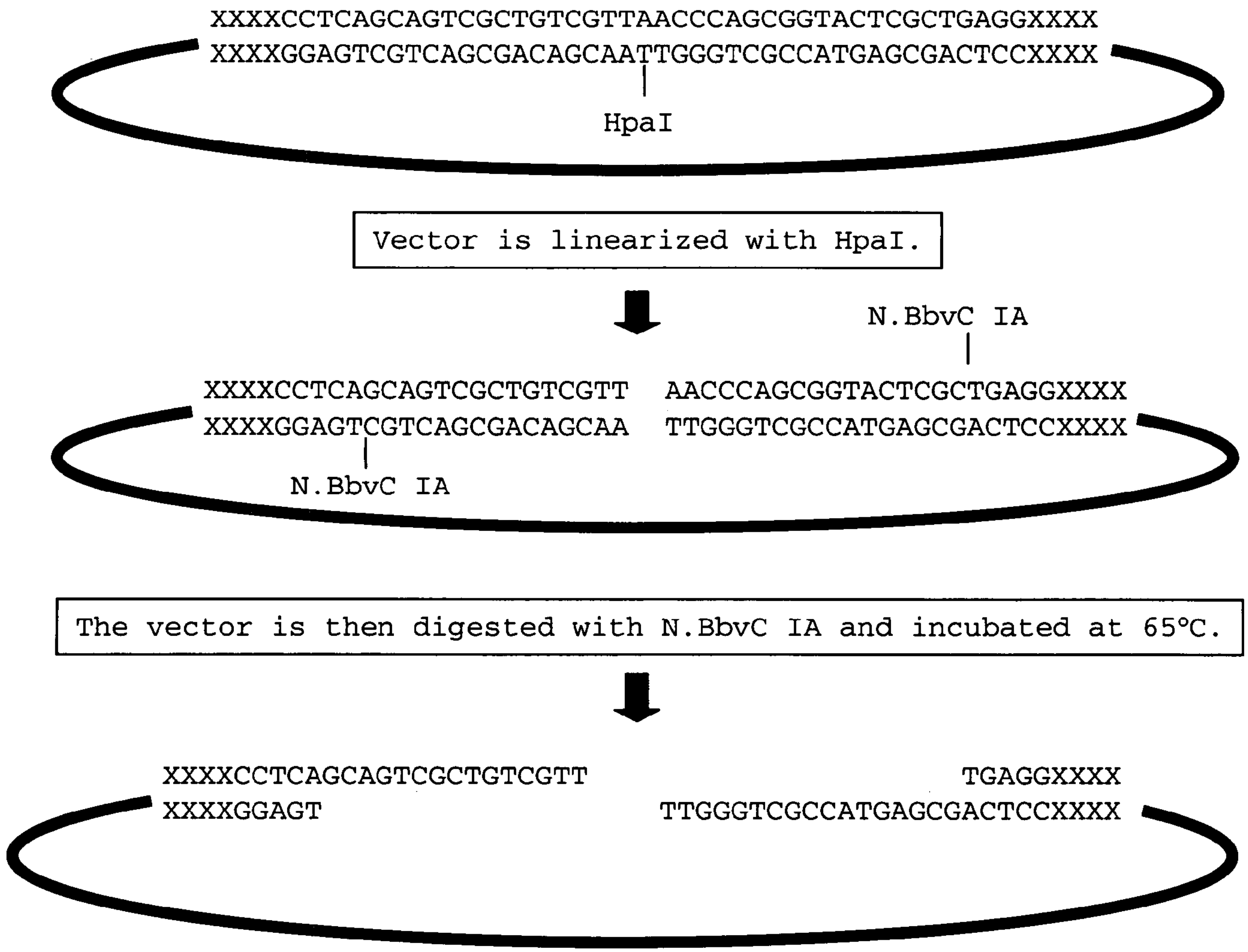
FIG. 3 illustrates the production of a plasmid vector with terminal, single-stranded segments. The single-stranded segments are comprised of SEQ ID NO:2 which is bisected after restriction endonuclease and nicking endonuclease digestion along with heating to remove the nicked short complementary strands, resulting in the production of the terminal, single-stranded segments.

This example illustrates the introduction of terminal, single-stranded DNA segments into a plasmid backbone. With reference to FIG. 3, a DNA adapter molecule, having the nucleotide sequence of SEQ ID NO:2, was inserted between an AgeI (ACCGGT) and a KpnI (GGTACC) restriction site in the plasmid of FIG. 2 using T4 DNA ligase (Invitrogen, Carlsbad, Calif.), inserting the adapter between promoter P-Os.Act) and the transcription termination sequence (T-St.Pis4). The resulting plasmid was linearized using the restriction endonuclease, HpaI (GTTAAC), then treated with the nicking endonuclease, N.BbvC IA (GCTGAGG). After digestion, the reaction was heated to 65 degree Celsius, causing the nicked strands of DNA to disassociate from their complementary DNA strands providing the resulting linearized, plasmid with two terminal, single-stranded DNA segments. Each terminal, single-stranded segment contained a unique sequence of nucleotides to allow assembly with another DNA molecule in a specific directionality.

Example 2

This example illustrates the addition of two, terminal, single-stranded DNA segments to a protein coding sequence for insertion into the plasmid that has been linearized with terminal single-stranded DNA segments.

Figure 5:
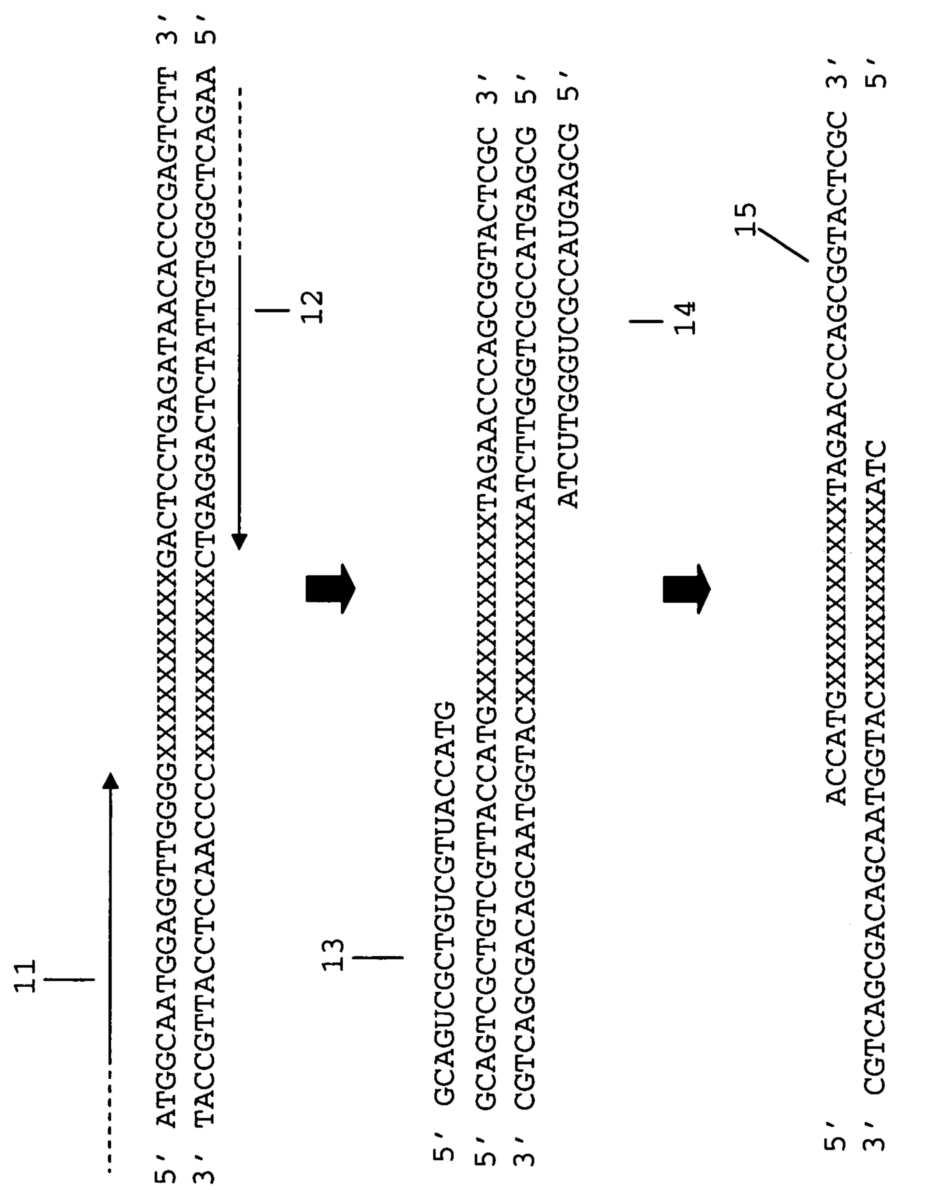
FIG. 5 illustrates PCR amplification to produce DNA with terminal, single-stranded segments using primers provided as SEQ ID NO: 4 and SEQ ID NO: 5, followed by PCR amplification using primers provided as SEQ ID NO: 6 and SEQ ID NO: 7.

DNA encoding the *Arabidopsis thaliana* protein for a conserved oligomeric Golgi complex component-related protein (CGPG3721) has the nucleotide sequence of SEQ ID NO:3. Polymerase chain reaction was employed to produce the terminal, single-stranded DNA segments in the DNA molecule encoding CGPG3721. As shown in FIG. 5 the sequence of the CGPG3721 coding sequence (SEQ ID NO:3) was used to design the primers with nucleotide sequence of SEQ ID NO: 4 (sense) and 5 (antisense). Each primer comprises one of two terminal, single-stranded DNA segments to be added to the CGPG3721 coding sequence (SEQ ID NO:3). The primers were designed as follows:

Sense Primer:

5'-GCAGTCGCTGTCGTTACCATGGCAATGGAGGTTGGGG-3'

Antisense Primer:

5'-GCGAGTACCGCTGGGTTCTAAGACTCGGGTGTTATCTCAGGAGTC-3' where, in each primer, the underlined portion of the sequence represents the region that will be made into a terminal, single-stranded DNA segment.

Polymerase chain reaction amplification was performed using a high fidelity thermal polymerase, KOD hot start DNA polymerase (Novagen, Madison Wis.). The polymerase chain reaction was performed in a 25 microliters (μl) volume containing, 1×KOD hot start DNA polymerase buffer, 1M Betaine (Sigma, St. Louis Mo.), 1 mM $MgSO_4$, 250 μM dNTPs, 5 pmols of each primer (primer molecules 11 and 12 in FIG. 5) and 1 unit of KOD hot start DNA polymerase. The polymerase chain reaction was performed in a PTC-225 DNA Engine Tetrad™ thermal cycler (MJ Research Inc., Waltham Mass.) using the following cycler parameters ("cycle parameter 1"):

1. 94 degree Celsius for 2 minutes
2. 94 degree Celsius for 15 seconds
3. 70 degree Celsius for 30 seconds (−1 degree Celsius per cycle)
4. 72 degree Celsius for 5 minutes
5. Go to step 2, 9 times
6. 94 degree Celsius for 15 seconds
7. 60 degree Celsius for 30 seconds
8. 72 degree Celsius for 5 minutes
9. Go to step 6, 24 times
10. 72 degree Celsius for 10 minutes
11. 10 degree Celsius forever
12. end A second round of polymerase chain reaction was performed to introduce uridine residues in the region in which the terminal, single-stranded DNA segments were produced (primer molecules 13 and 14 in FIG. 5). Many DNA polymerases are unable to read uridine residues in the template strand of DNA or are unable to polymerize strands using uridine residues. Polymerase chain reaction was therefore performed using an enzyme capable of incorporating and reading uridines, Expand High Fidelity$^{plus}$ PCR System (Roche, Indianapolis Ind.). The primers designed as the second pair of oligonucleotide primers comprising the two terminal, single-stranded DNA segments are provided as SEQ ID NOS: 6 (sense) and 7 (antisense). The primers were designed as follows:

Sense:
5'-GCAGUCGCTGUCGTUACCATG-3'
Antisense:
5'-GCGAGUACCGCUGGGTUCTA-3'

The polymerase chain reaction was performed in a 25 μl volume containing, 1× Expand High Fidelity$^{plus}$ polymerase chain reaction buffer, 1.5 mM $MgCl_2$, 200 μM dNTPs, 5 pmols of each primer, 5 units of Expand High Fidelity$^{plus}$ Enzyme Blend and 1 μl of the first polymerase chain reaction product. The polymerase chain reaction was performed in a PTC-225 DNA Engine Tetrad™ thermal cycler using the following cycler parameters ("cycle parameter 2"):

1. 94 degree Celsius for 2 minutes
2. 94 degree Celsius for 30 seconds
3. 55 degree Celsius for 30 seconds
4. 72 degree Celsius for 4 minutes
5. Go to step 2, 14 times
6. 72 degree Celsius for 10 minutes
7. 10 degree Celsius forever
8. End Terminal, single-stranded DNA segments on DNA coding for CGPG3721 were produced by treating the product of the second polymerase chain reaction with Uracil-DNA Glycosylase (New England Biolabs Inc., Beverly, Mass.). The Uracil-DNA Glycosylase reaction was performed in a 10 μl volume containing, 5 μl of the second polymerase chain reaction product, 3.5 μl of deionized water, 0.5 μl 5× Expand High Fidelity$^{plus}$ polymerase chain reaction buffer (containing 7.5 mM $MgCl_2$), and 1 μl of Uracil-DNA Glycosylase (2 units of enzyme). The Uracil-DNA Glycosylase reaction was performed in a PTC-225 DNA Engine Tetrad™ thermal cycler at 37 degree Celsius for 1 hour.

Example 3

This example illustrates the assembly of a DNA construct. With reference to FIG. 6 the plasmid illustrated in FIG. 4 was prepared by assembling the linearized plasmid 16 which was prepared in Example 1 and the DNA molecule 15, presented as SEQ ID NO: 36 (represented by nucleotide 10,258 through nucleotide 1 of the plasmid presented as SEQ ID NO: 8) which was modified with terminal single-stranded DNA segments in Example 2. One microliter of the linearized plasmid (25 nanograms (ng)) was added to the Uracil-DNA Glycosylase reaction product prepared in Example 2 and incubated in a PTC-225 DNA Engine Tetrad™ thermal cycler using the following cycler parameters ("cycle parameter 3"):

1. 65° for 5 minutes
2. −0.1°/sec to 37° C.
3. 37° C. forever
4. End

Figure 4:
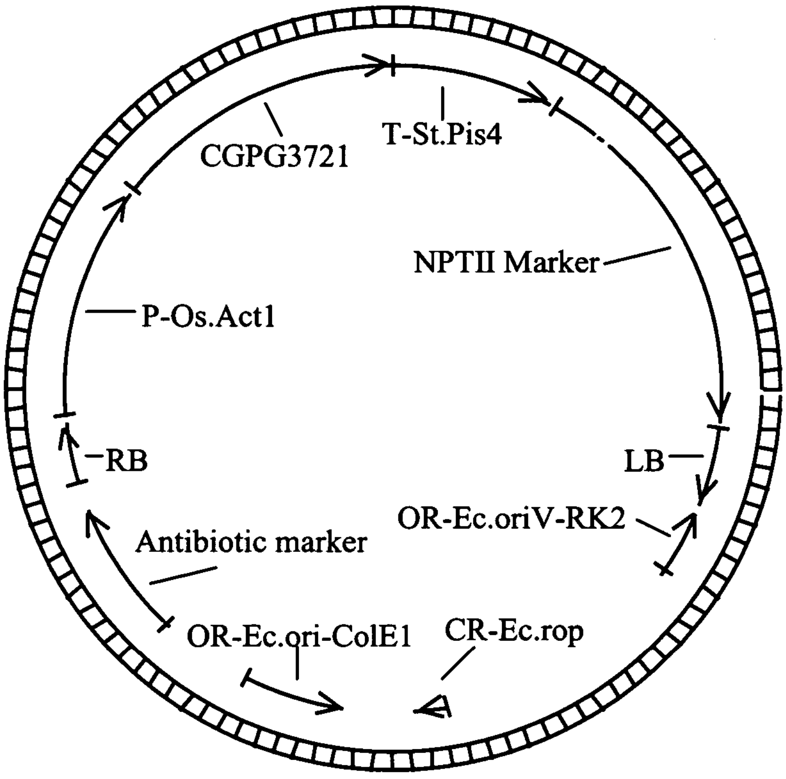
FIG. 4 illustrates a DNA construct assembled from two DNA molecules and is Presented as SEQ ID NO: 8.

The assembled DNA construct was transformed into ElectroMAX™ DH10B competent cells (Invitrogen, Carlsbad Calif.). A 0.5 μl aliquot from the assembly reaction was mixed with 20 μl of ElectroMAX™ DH 10B competent cells on ice and loaded into a MicroPulser 0.2 mm electroporation cuvette (Bio-Rad Laboratories Inc., Hercules Calif.) for electroporation. The cells were transformed by electroporation using 1.8 kV with a 165-2100 MicroPulser Electroporator (Bio-Rad Laboratories Inc., Hercules Calif.). The transformed cells were incubated in 180 μl of SOC medium (Invitrogen Inc., Carlsbad Calif.) at 37 degree Celsius for 1 hour. The cells were then plated onto LB agar plates containing spectinomycin (75 mg/1) and grown overnight at 37 degree Celsius. Colonies of transformed cells were selected and grown in LB media overnight at 37 degree Celsius. The plasmid DNA construct was isolated using the QIAprep® Spin Miniprep Kit (QIAgen Sciences, Valencia Calif.). DNA sequencing was performed on an Applied Biosystems 3730×1 DNA Analyzer, using Big Dye® Terminator v3.0 for sequence validation. The nucleotide sequence of the assembled plasmid show in FIG. 4 is SEQ ID NO: 8.

Example 4

This example illustrates the assembly of a DNA construct with an inverted repeat, using three DNA molecules each having terminal single-stranded DNA segments. One molecule is a linearized plasmid prepared essentially by the method illustrated in Example 1. The other two molecules were amplified from the same coding sequence but assembled in a manner to allow the production of an inverted repeat. The region between the repeats was produced from terminal, single-stranded DNA segments, resulting in a region between the repeats with restriction endonuclease sites.

Figure 7:
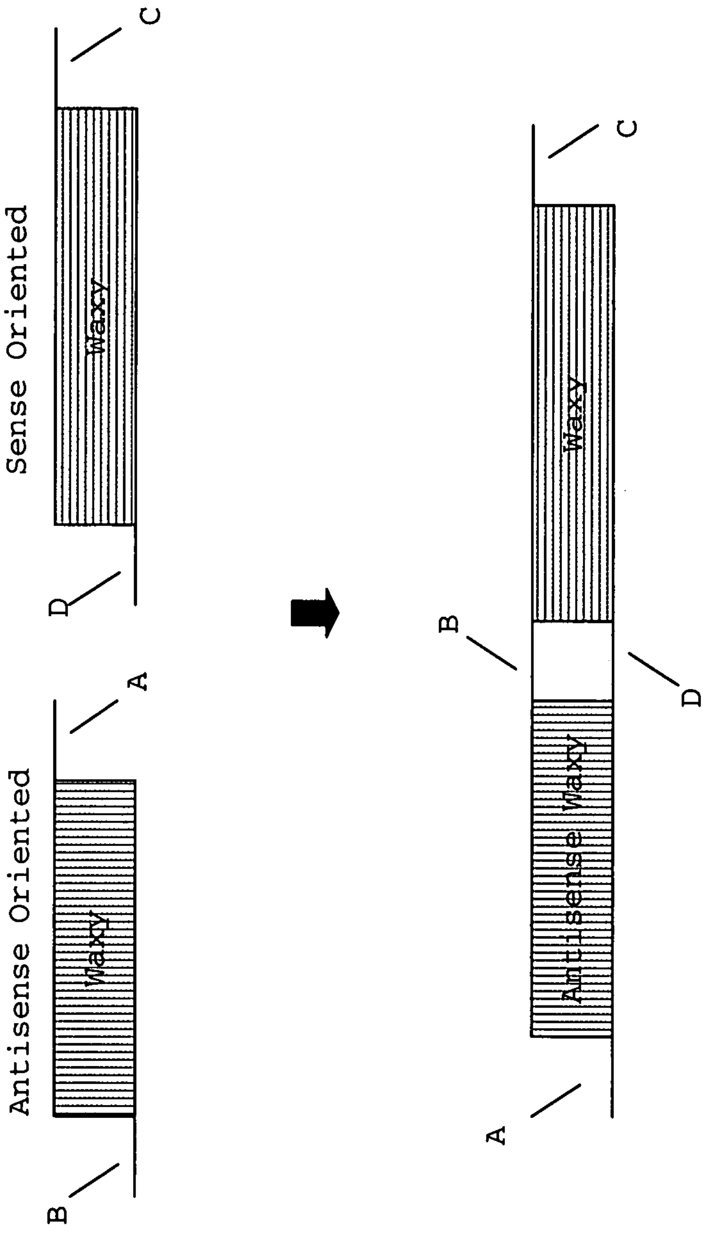
FIG. 7 illustrates an amplification and assembly scheme for producing an inverted repeat. The terminal, single-stranded DNA segments A. B. C and D in the two Waxy DNA molecules are produced using the primers presented as SEQ ID NOS: 10 and 14 (for terminal, single-stranded DNA segment A); SEQ ID NOS: 11 and 15 (for terminal, single-stranded DNA segment B); SEQ ID NOS: 13 and 17 (for terminal, single-stranded DNA segment C) and; SEQ ID NOS: 12 and 16 (for terminal, single-stranded DNA segment D).

With reference to FIG. 7 an inverted repeat DNA molecule with terminal, single-stranded DNA segments was prepared from DNA coding for maize granule-bound glycogen synthase, which is referred to as "Waxy". PCR was employed to produce unique terminal, single-stranded DNA segments on separate DNA molecules which were designed to be assembled in an inverted repeat of Waxy DNA. The Waxy DNA sequence which was used for primer design is provided as SEQ ID NO:9. The primers designed as the first two pairs of oligonucleotide primers comprising the two terminal, single-stranded DNA segments of each DNA molecule were designed as follows:

SEQ ID NO: 10—Sense primer, Waxy 3

5'-<u>AAGTACTGCGATCGCGTTAACGCT</u>AGATTCAAGTCGTCCTTCGATTT
CATCG-3'

SEQ ID NO: 11—Antisense primer, Waxy 1

5'-GCAGTCGCTGTGCGATACCACGTCGGGGCCCTTCTGCTCTTCCA-3'

SEQ ID NO: 12—Sense primer, Waxy 2

5'-AGCGTTAACGCGATCGCAGTACTTGAAGCTCCAAGGATCCTGAGCCT CAAC-3'

SEQ ID NO: 13—Antisense primer, Waxy 4

5'-GCGAGTACCGCTGGCGATCTAACGTCGGGGCCCTT CTGCTCTTCC-3' where, in each primer, the underlined portion of the sequence represents the region that will be made into a terminal, single-stranded DNA segment. Polymerase chain reaction amplification was performed essentially as described in Example 2 using cycle parameter 1. A second round of polymerase chain reaction was performed to introduce uridine residues in the region in which the terminal, single-stranded DNA segments were produced. Polymerase chain reaction was performed as previously described in Example 2 using cycle parameter 2. The primers designed as the second pair of oligonucleotide primers comprising the two terminal, single-stranded DNA segments were designed as follows:

SEQ ID NO: 14—Sense primer, Waxy 3U

5'-AAGUACTGCGAUCGCGTUAACGCU-3'

SEQ ID NO: 15—Antisense primer, Waxy 1U

5'-GCAGUCGCUGUGCGAUACC-3'

SEQ ID NO: 16—Sense primer, Waxy 2U

5'-AGCGTUAACGCGAUCGCAGUACUU-3'

SEQ ID NO: 17—Antisense primer, Waxy 4U

5'-GCGAGUACCGCUGGCGAUCTA-3'

The terminal, single-stranded DNA segments A, B, C and D in the two Waxy DNA molecules were produced by treating equal molar amounts of the products of the second polymerase chain reaction with Uracil-DNA glycosylase and assembled essentially as described in Example 3 using cycle parameter 3, where single-stranded DNA segment A is complementary to single-stranded DNA segment D allowing assembly of the antisense and sense oriented Waxy segments into an inverted repeat construct.

Following assembly of the Waxy inverted repeat, the inverted repeat and the linearized plasmid, each having terminal, single-stranded DNA segments, were assembled essentially as described in Example 3 using cycle parameter 3. The final assembled DNA construct as shown in FIG. 8 comprised the elements described in Table 2 where the position is indicated by reference to SEQ ID NO: 18.

TABLE 2

| Element Name | Position | Element Function |
|---|---|---|
| RB | 11493-11823 | Right border sequence for T-DNA transfer. |
| P-Zm.SzeinC1 | 1-1909 | Promoter elements from the 27 KDa storage protein zein gene from Maize including 5'UTR and an enhancer intron from the *Zea mays* HSP70 intron with flanking exon enhancer sequence. |
| CR-Zm.Waxy AS | 1943-2577 | Antisense coding region of the *Zea mays* Waxy gene. |
| Spacer | 2578-2601 | Spacer region, SEQ ID NO: 19. |
| CR-Zm.S Waxy | 2602-3002 | Sense coding region of the *Zea mays* Waxy gene. |
| T-St.Pis4 | 3044-3896 | Transcription termination sequence of the potato proteinase inhibitor II gene. |
| nptII marker | 4031-5476 | Transcription unit for nptII marker including CaMV 35S promoter, coding region for nptII and nos transcription termination sequence. |
| IG-St.Pis4 | 5488-6234 | Intergenic region of the potato proteinase inhibitor II gene used for marker excision. |
| LB | 6297-6738 | Left border sequence for T-DNA transfer. |
| OR-Ec.oriV-RK2 | 6825-7221 | Vegetative origin of replication used by *Agrobacterium tumefaciens*. |
| CR-Ec.rop | 8730-8921 | Coding region for the repressor of the primer for the ColE1 origin of replication. |
| OR-Ec.ori-ColE1 | 9439-9937 | Minimal origin of replication from the *Escherichia coli* plasmid ColE1 used for replication in *E. coli*. |
| Antibiotic marker | 10468-11356 | Transcription unit for antibiotic resistance. |

The assembled DNA construct was transformed into ElectroMAX™ DH10B competent cells as previously described in Example 3.

Sequencing through an inverted repeat results in contamination of the sequence chromatogram due to false priming within the inverted repeat. Therefore, it becomes necessary to linearize the inverted repeat between the repeats prior to sequencing. In the present example, the terminal, single-stranded DNA segments that were used to assemble the Waxy inverted repeat were designed to contain three restriction endonuclease sites which were not present in the plasmid backbone, containing terminal, single-stranded DNA segments or the regions of DNA encoding the Waxy protein. The region between the repeats (referred herein as TAGART.Spacer Region 2) is illustrated in FIG. 9 and provided as SEQ ID NO: 19. Two digestion reactions were performed on the assembled construct, pMON94750 using HpaI (GTTAAC) and AsiSI (GCGATCGC) and 400 ng of pMON94750 per reaction. After digestion, the linearized construct was precipitated. DNA sequencing confirmation was performed on an Applied Biosystems 3730×1 DNA Analyzer, using Big Dye® Terminator v3.0 using sequencing primers designed to read from the HSP70 intron and the Pis4 terminator through the Waxy inverted repeat. Using sequence data from both digestions, the full sequence of the Waxy inverted repeat was determined.

Example 5

This example illustrates an alternative assembly of a DNA construct useful for gene suppression of the Waxy gene with a spacer inserted between the anti-sense and sense segment of the Waxy gene.

Figure 10A:
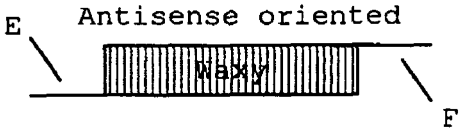
FIG. 10*a* illustrates an antisense molecule with terminal, single-stranded DNA segments. The terminal, single-stranded DNA segments E and F are produced using the primers presented as SEQ ID NOS: 21 and 23 (for terminal, single-stranded DNA segment E) and SEQ ID NOS: 20 and 22 (for terminal, single-stranded DNA segment F).

With reference to FIG. 10*a* an anti-sense segment of Waxy coding region of about 635 nt (indicated as "CR-Zm.Waxy AS" in Table 3 and in the construct illustrated in FIG. 12) is amplified from the Waxy gene by PCR followed by uracil-DNA glycosylase treatment to produce unique terminal, single-stranded DNA segments E and F. More specifically, the segment for the anti-sense oriented Waxy is cloned using a sense primer (SEQ ID NO:20) and an anti-sense primer (SEQ ID NO:21), where the first 16 and 24 nucleotides of each primer, respectively are designed for single-stranded DNA segments. Polymerase chain reaction amplification is performed essentially as described in Example 2 using cycle parameter 1. A second round of polymerase chain reaction is performed to introduce uridine residues in the region in which the terminal, single-stranded DNA segments are produced. Polymerase chain reaction is performed as previously described in Example 2 using cycle parameter 2. The primers designed as the second pair of oligonucleotide primers comprising the two terminal, single-stranded DNA segments of the antisense DNA molecule are designed as follows:

SEQ ID NO: 22—Sense primer

```
5'-GCAGUCGCUGUGCGAUACC-3'
```

SEQ ID NO: 23—Anti-sense primer

```
5'-AGCGUUAACGCGAUCGCAGUACUU-3'
```

The terminal, single-stranded DNA segments in the anti-sense segment of Waxy are produced by treating equal molar amounts of the product of the second polymerase chain reaction with Uracil-DNA glycosylase essentially as described in Example 3 using cycle parameter 3.

Figure 10B:
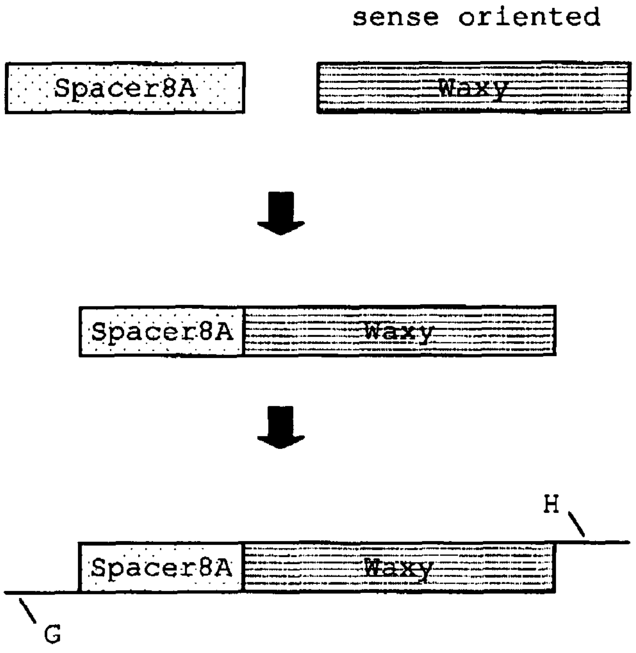
FIG. 10*b* illustrates an amplification scheme for making a fusion amplicon with terminal, single-stranded DNA segments. The terminal, single-stranded DNA segments G and H are produced using the primers presented as SEQ ID NO: 27 (for terminal, single-stranded DNA segment G) and SEQ ID NOS: 25 and 28 (for terminal, single-stranded DNA segment H).

With reference to FIG. 10*b* a sense segment of Waxy coding region of about 400 nt (indicated as "CR-Zm.Waxy S" in Table 3 and in the construct illustrated in FIG. 12) is amplified from the same part of the Waxy gene and is fused to a 150 nt "Spacer" having sense sequence of SEQ ID NO: 26 to form a fusion amplicon with unique terminal single-stranded DNA segments G and H. More specifically, the sense segment of Waxy is cloned using a sense primer (SEQ ID NO: 24) and an anti-sense primer (SEQ ID NO: 25), where the first 18 nucleotides of the sense primer are homologous to the 3' end of the Spacer and where the 18 nucleotides of the anti-sense primer is designed for a single-stranded segment. Polymerase chain reaction amplification is performed essentially as described in Example 2 using cycle parameter 1. The Spacer is synthesized from a synthetic primer of SEQ ID NO:26 and a complementary primer and used in the second round of polymerase chain reaction which produces a fusion amplicon of the Spacer and sense segment of Waxy, followed by introducing uridine residues in the region in which the terminal, single-stranded DNA segments are produced. The primers designed as the second pair of oligonucleotide primers comprising the two terminal, single-stranded DNA segments G (complementary to F) and H of the fusion amplicon are designed as follows:

SEQ ID NO: 27 Sense Primer

```
5'-AAGUACTGCGAUCGCGUUAACGCU-3'
```

SEQ ID NO: 28—Antisense primer

```
5'-GCGAGUACCGCUGGCGAUCTA-3'
```

The polymerase chain reaction is performed in a 30 μl volume containing, 1× Expand High Fidelity$^{plus}$ polymerase chain reaction buffer, 1.5 mM $MgCl_2$, 200 μM dNTPs, 5 pmols of each primer, 5 units of Expand High Fidelity$^{plus}$ Enzyme Blend, 1 μl of the first polymerase chain reaction sense DNA molecule product and 1 μl of Spacer molecule (10 ng). The polymerase chain reaction is performed in a PTC-225 DNA Engine Tetrad™ thermal cycler using the following cycler parameters ("cycle parameter 4"):

1. 94 degree Celsius for 2 minutes
2. 94 degree Celsius for 15 seconds
3. 62 degree Celsius for 30 seconds (−1 degree Celsius/cycle)
4. 72 degree Celsius for 3 minutes
5. Go to step 2, 12 times
6. 94 degree Celsius for 15 seconds
7. 50 degree Celsius for 30 seconds
8. 72 degree Celsius for 3 minutes
9. Go to step 6, 15 times
10. 72 degree Celsius for 5 minutes
11. 10 degree Celsius forever
12. End The terminal, single-stranded DNA segments in the fusion amplicon are produced by treating equal molar amounts of the product of the second polymerase chain reaction with Uracil-DNA glycosylase. The anti-sense segment with terminal single-stranded DNA segments E and F and the fusion amplicon with terminal single-stranded DNA segments G and H are assembled essentially as described in Example 3 using cycle parameter 3. The assembled inverted repeat molecule is shown in FIG. 11 with remaining terminal single-stranded DNA segments E and H.

The assembled inverted repeat molecule and a linearized plasmid, each having terminal, single-stranded DNA segments, are assembled essentially as described in Example 3 using cycle parameter 3. The final assembled DNA construct as shown in FIG. 12 comprise the elements described in Table 3 where the position is indicated by reference to SEQ ID NO: 29.

TABLE 3

| Element Name | Position | Element Function |
|---|---|---|
| RB | 11493-11823 | Right border sequence for T-DNA transfer. |
| P-Zm.SzeinC1 | 1-1909 | Promoter elements from the 27 KDa storage protein zein gene from Maize including 5'UTR and an enhancer intron from the *Zea mays* HSP70 intron with flanking exon enhancer sequence. |
| CR-Zm.Waxy AS | 1943-2578 | Antisense coding region of the *Zea mays* Waxy gene. |
| Spacer | 2579-2728 | Spacer region, SEQ ID NO: 26. |
| CR-Zm.Waxy S | 2729-3129 | Sense coding region of the *Zea mays* Waxy gene. |
| T-St.Pis4 | 3171-4024 | Transcription termination sequence of the potato proteinase inhibitor II gene. |
| nptII marker | 4158-5603 | Transcription unit for nptII marker including CaMV 35S promoter, coding region for nptII and nos transcription termination sequence. |
| IG-St.Pis4 | 5615-6361 | Intergenic region of the potato proteinase inhibitor II gene used for marker excision |
| LB | 6406-6865 | Left border sequence for T-DNA transfer. |
| OR-Ec.oriV-RK2 | 6952-7348 | Vegetative origin of replication used by *Agrobacterium tumefaciens*. |
| CR-Ec.rop | 8897-9048 | Coding region for the repressor of the primer for the ColE1 origin of replication. |

TABLE 3-continued

| Element Name | Position | Element Function |
|---|---|---|
| OR-Ec.ori-ColE1 | 9566-10064 | Minimal origin of replication from the *Escherichia coli* plasmid ColE1 used for replication in *E. coli*. |
| Antibiotic marker | 10595-11483 | Transcription unit for antibiotic resistance. |

The assembled DNA construct is transformed into Electro-MAX™ DH10B competent cells as previously described in Example 3.

One skilled in the art will recognize that other cycle parameters can be employed in the polymerase chain reaction amplifications and the Uracil-DNA Glycosylase reaction without departing from the scope and spirit of the present invention. The present invention can be performed within a wide range of equivalent parameters. The present invention is intended to cover any uses, variations, or adaptations of the invention following the principles of the invention in general.

What is claimed is:

1. A method for assembling a DNA construct of DNA molecules with a substantially identical DNA segment in an inverted repeat of said substantially identical DNA segment, said method comprising:

a) providing at least two double-stranded DNA molecules, wherein each molecule has terminal, single-stranded, DNA segments in a length of from 10 to 30 nucleotides extending from the 3' termini; wherein terminal, single-stranded DNA segments on each double-stranded DNA molecule do not hybridize to each other; wherein a terminal, single-stranded DNA segments on a first double-stranded DNA molecule and a terminal, single-stranded DNA segments extending from a second double-stranded DNA molecule hybridize to each other to allow for specific annealing and linkage of the first and second DNA molecules in a predetermined order; and wherein said first and second double-stranded DNA molecules comprise a substantially identical DNA segment; in reverse complement order and wherein one of said double-stranded DNA molecules comprises a spacer region of DNA that is not substantially identical with DNA in the other molecule;

b) incubating said DNA molecules under conditions suitable to promote the specific annealing and assembling of the DNA molecules to provide a construct of said molecules wherein said substantially identical DNA elements are arranged as inverted repeat segments; and c) wherein the spacer region is between the first and second double-stranded DNA molecules and comprises restriction endonuclease sites permitting the digestion of inverted repeat segments to facilitate DNA sequencing of said inverted repeat segments.

* * * * *